(12) United States Patent
Zeiller et al.

(10) Patent No.: US 6,528,538 B1
(45) Date of Patent: Mar. 4, 2003

(54) CYCLIC COMPOUNDS USEFUL IN THE TREATMENT OF DYSLIPIDAEMIA, ATHEROSCLEROSIS AND DIABETES, PHARAMACEUTICAL COMPOSITIONS AND PREPARATION PROCESS

(75) Inventors: Jean-Jacques Zeiller; Jean-Jacques Berthelon, both of Lyons (FR); Eric Raspé, Mouscron (BE); Daniel Guerrier, Saint Genis Laval (FR)

(73) Assignee: Merck Patentgesellschaft, Darmstadt (DE)

( * ) Notice: Subject to any disclaimer, the term of this patent is extended or adjusted under 35 U.S.C. 154(b) by 0 days.

(21) Appl. No.: 09/743,759

(22) PCT Filed: Jul. 9, 1999

(86) PCT No.: PCT/EP99/04831

§ 371 (c)(1),
(2), (4) Date: Jan. 16, 2001

(87) PCT Pub. No.: WO00/04011

PCT Pub. Date: Jan. 27, 2000

(30) Foreign Application Priority Data

Jul. 17, 1998 (FR) ............................................. 98 09164

(51) Int. Cl.$^7$ ............................................. A61K 31/335
(52) U.S. Cl. ........................ 514/452; 514/326; 514/414; 546/207; 568/811; 568/812; 549/336; 549/290; 549/373; 549/374; 549/375
(58) Field of Search .................................. 549/336, 374, 549/375, 373, 290; 548/465; 546/207; 514/452, 414, 326; 568/811, 812

(56) References Cited

U.S. PATENT DOCUMENTS 4,032,536 A   6/1977 Raeymaekers et al.

FOREIGN PATENT DOCUMENTS

EP   0471493   2/1992
EP   0507291   10/1992

OTHER PUBLICATIONS

Christian S. Rondestvedt Jr.: "M-dioxanes and other cyclic acetals" *Journal of Organic Chemistry* vol. 26, No. 7, Jul. 25, 1961 pp. 2247–2253.
Chem Abstracts, vol. 86, No. 7, (Feb. 14, 1977) No. 43057s (V.E. Kataev et al.) & Bull. Soc. Chim.elg., vol. 85, No. 3, 1976, pp 103–113.
Chem Abstracts, 13$^{th}$ collective Index, Chemical Substances3 : Diazabicycloo . . . Dobon, vol. 116–125, 1992–1996 pp. 1034, col. 1, line62– col. 3, line 2 pp 1042.
Dr. Otto–Albrecht Neumuller: "Rompps Chemie–Lexikon (8 Auflage)" 1981, W. Keller & Co. pp. 842, col. 2, line 6–p. 843, col. 1, line 11.
C. Tschierske, H. Kohler, H. Zaschke and E. Kleinpeter "The Anomeric Effect of the Carboethoxy Group in Oxygen and Sulphur Containing Heterocycles" Tetrahedron vol. 45, No. 22, pp. 6987, to 6998, 1989 Printed in Great Britain.
W.J. Croxall, J. O. Van Hook and R. Luckenbaugh Transetherification Reactions. Glycols with Certain β–Alkoxy Esters vol. 71; pp. 2741–2742; published in Philadelphia, PA.
William F. Bailey and Ernest I. Eliel Conformational Analysis. XXIX. 2–Substituted and 2,2–Disubstituted 1,3–Dioxanes. The Generalized and Reverse Anomeric Effects Journal of the American Chemical Society; p. 17981806; Mar. 20, 1974.
Yutaka Honda and Gen–Ichi Tsuchihashi Substitution–Type Thermal 1, 2–Rearrangement. Synthesis of Chiral β–Aryl(or Alkenyl)α The Chemical Society of Japan, 1987; vol. 60, No. 7 pp. 2698–2700.
E.I. Ryumtsev, N.P. Evlampieva, and A.P. Kovshik Dipole and Electrooptical Properties of Liquid–Crystal Molecules with 1, 3–Dioxane Cycles Russian Journal of Physical Chemistry, vol. 71, No. 2, 1997, pp. 295–298.
D.L. Rakhmankulov, S.S. Zlotskii and V.N. Uzikova Radical Transformations of Bis–1, 3–Dioxacyclanes 1975 Plenum Publishing Corporation, p. 2646.

*Primary Examiner*—Amelia Owens
(74) *Attorney, Agent, or Firm*—Millen, White, Zelano & Branigan, P.C.

(57) ABSTRACT

The present invention relates to cyclic compounds which are of the class of compounds of formula I wherein X and Y represent an oxygen atom and to processes for preparing such compounds. The compounds are useful in the treatment of dyslipidemia, atherosclerosis, and diabetes.

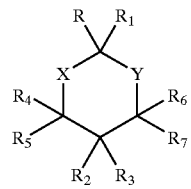

15 Claims, 1 Drawing Sheet

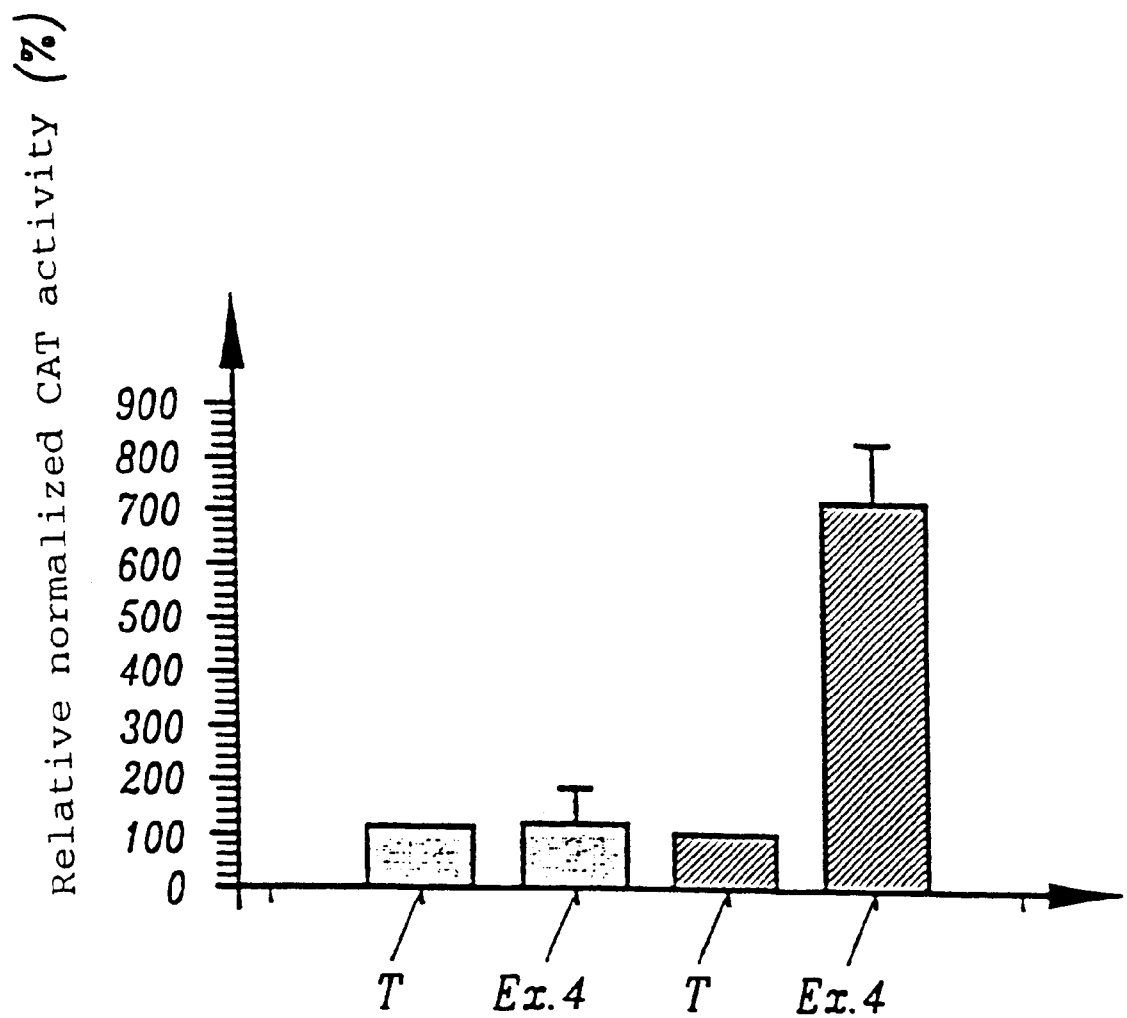

CYCLIC COMPOUNDS USEFUL IN THE TREATMENT OF DYSLIPIDAEMIA, ATHEROSCLEROSIS AND DIABETES, PHARAMACEUTICAL COMPOSITIONS AND PREPARATION PROCESS

The present invention relates to cyclic compounds which can be used in the treatment of dyslipidaemia, atherosclerosis and diabetes, to pharmaceutical compositions containing them and to processes for preparing these compounds.

The invention also relates to the use of these compounds for the production of medicinal products intended for the treatment of dyslipidaemia, atherosclerosis and diabetes.

In most countries, cardiovascular disease remains one of the main diseases and the main cause of mortality. About a third of men develop a major cardiovascular disease before the age of 60, women showing a lower risk (ratio of 1 to 10). This disease becomes even more prevalent with age (after the age of 65, women become just as vulnerable to cardiovascular disease as men). Vascular diseases such as coronary disease, cerebrovascular accidents, restenosis and peripheral vascular disease remain the main cause of mortality and handicap throughout the world.

Although the diet and the lifestyle can accelerate the development of cardiovascular diseases, a genetic predisposition leading to dyslipidaemia is a significant factor in cardiovascular attacks and death.

The development of atherosclerosis appears to be linked mainly to dyslipidaemia, which means abnormal levels of lipoproteins in the blood plasma. This dysfunction is particularly evident in coronary disease, diabetes and obesity.

The concept intended to explain the development of atherosclerosis has mainly been focused on the metabolism of cholesterol and on the metabolism of triglycerides.

However, since the research studies by Randle et al. (Lancet, 1963, 785–789), an original concept has been proposed: a glucose-fatty acid cycle or Randle cycle, which describes regulation of the equilibrium between the metabolism of lipids, in terms of triglycerides and cholesterol, and the oxidation of glucose. According to this concept, the inventors have developed an original programme, the aim of which is to find novel compounds which act simultaneously on the metabolism of lipids and glucose.

Fibrates are well-known therapeutic agents with a mechanism of action via the "Peroxisome Proliferator Activated Receptors". These receptors are the main regulators of lipid metabolism in the liver (PPARα isoform). In the last ten years, thiazolidinediones have been described as powerful hypoglycaemiant agents in animals and man. It has been reported that thiazolidinediones are powerful selective activators of another form of PPARs: PPARγ (Lehmann et al., J. Biol. Chem., 1995, 270, 12953–12956).

The inventors have discovered a novel class of compounds which are powerful activators of the PPARα and PPARγ isoforms. On account of this activity, these compounds have a substantial hypolipidaemiant and hypoglycaemiant effect.

The compounds of the invention correspond to formula I below:

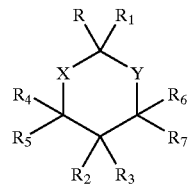

in which

X and Y represent, independently of each other, a methylene group; an oxygen or sulphur atom; or —$NR_a$— in which $R_a$ represents a hydrogen atom, a ($C_1$–$C_7$)alkyl, ($C_6$–$C_{10}$) aryl group or a 3- to 10-membered heterocycle comprising 1 to 4 endocyclic hetero atoms chosen from O, S and N; the said aryl group and the said heterocycle optionally being substituted with one or more radicals Z as defined below;

R represents a hydrogen atom; a ($C_1$–$C_7$)alkyl group; a phthalamido ($C_1$–$C_7$) alkyl group; ($C_3$–$C_{12}$) cycloalkyl; a group —$(CH_2)_p$—$COOR_b$ in which p is an integer from 0 to 6 and $R_b$ represents a hydrogen atom or a ($C_1$–$C_7$) alkyl group; a ($C_6$–$C_{10}$)aryl group; a 3- to 10-membered heterocycle comprising 1 to 4 endocyclic hetero atoms chosen from O, S and N; a ($C_6$–$C_{10}$)aryl($C_1$–$C_7$)alkyl group; it being understood that the aryl groups present in R and the said heterocycle are optionally substituted with one or more substituents chosen from a radical Z as defined below and a ($C_1$–$C_7$)alkylene chain;

$R_1$ represents a hydrogen atom; a ($C_1$–$C_7$)alkyl group; ($C_1$–$C_7$)hydroxyalkyl; a ($C_6$–$C_{10}$)aryl group optionally substituted with one or more radicals W as defined below; a group —$P(O)$ $(OR_8)$ $(OR_9)$ in which $R_8$ and $R_9$ are, independently, a hydrogen atom or a ($C_1$–$C_7$)alkyl group; a group —$(CH_2)_t$—$COOR_c$ in which t is an integer from 0 to 6 and $R_c$ represents a hydrogen atom or a ($C_1$–$C_7$) alkyl group; a group —$CONR_{10}R_{11}$ in which $R_{10}$ and $R_{11}$ independently represent a hydrogen atom, a ($C_1$–$C_7$)alkyl group, a group $R_dO$—$CO$—($C_1$–$C_7$)alkyl in which $R_d$ represents H or ($C_1$–$C_7$)alkyl, or alternatively $R_{10}$ and $R_{11}$ together form a —$(CH_2)$ chain in which r is an integer equal to 4, 5 or 6;

$R_2$ and $R_3$ independently represent a hydrogen atom; a ($C_1$–$C_7$)alkyl group; ($C_3$–$C_{12}$)cycloalkyl; ($C_6$–$C_{10}$)aryl; ($C_6$–$C_{10}$)aryl($C_1$–$C_7$)alkyl; a 3- to 10-membered heterocycle comprising 1 to 4 endocyclic hetero atoms chosen from O, N and S; or a fluorenyl group; the said aryl groups present in $R_2$ or $R_3$, the said heterocycle and the said fluorenyl optionally being substituted with one or more radicals Z as defined below;

or alternatively $R_2$ and $R_3$ together form a chain —$(CH_2)_{r1}$ in which r1 is an integer equal to 2, 3, 4 or 5;

or alternatively $R_2$ and $R_3$ together form the group (a):

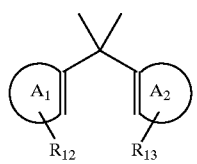

in which $A_1$ and $A_2$ independently represent ($C_6$–$C_{10}$)aryl or a 5- to 10-membered aromatic heterocycle comprising 1 to 4 endocyclic hetero atoms chosen from N, O and S, the said aryl group and the said heterocycle optionally bearing, in addition to the substituents $R_{12}$ and $R_{13}$, one or more other substituents chosen from the radicals Z as defined below; and in which $R_{12}$ and $R_{13}$ together form a chain

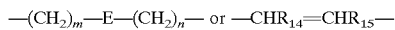

in which m and n are, independently, an integer from 0 to 6; E represents a bond, O, S, —$NR_e$—, in which $R_e$ represents a hydrogen atom or $(C_1-C_7)$alkyl or alternatively E represents a $(C_1-C_7)$alkylene or $(C_6-C_{10})$ arylene chain or a 3- to 10-membered divalent heterocyclic radical comprising 1 to 4 endocyclic hetero atoms chosen from O, N and S; and $R_{14}$ and $R_{15}$ are chosen, independently, from a hydrogen atom, $(C_1-C_7)$alkyl and $(C_6-C10)$aryl;

$R_4, R_5, R_6$ and $R_7$ independently represent a hydrogen atom; $(C_1-C_7)$alkyl; $(C_6-C10)$aryl optionally substituted with one or more radicals Z as defined below; or a 3- to 10-membered heterocycle comprising 1 to 4 endocyclic hetero atoms chosen from O, N and S, the said heterocycle optionally being substituted with one or more radicals Z as defined below;

Z is chosen from a halogen atom; a hydroxyl group; nitro; cyano; phenyl; phenyl $(C_1-C_7)$ alkyl; trifluoromethoxy; $(C_1-C_7)$ alkyl optionally substituted with one or more halogen atoms; $(C_1-C_7)$alkoxy; $(C_1-C_7)$alkylthio; $(C_2-C_7)$acylthio; $(C_1-C_7)$alkylsulphonyl; $(C_1-C_7)$ alkylsulphinyl; carbamoyl; N—$(C_1-C_7)$alkylcarbamoyl; N,N-di$(C_1-C_7)$alkylcarbamoyl; $(C_1-C_7)$ alkylamino; di($C_1-C_7$) alkylamino; a group —A—$COOR_f$ in which $R_f$ represents a hydrogen atom or a $(C_1-C_7)$alkyl group and A represents $(C_1-C_7)$alkylene, $(C_2-C_7)$ alkenylene, $(C_1-C_7)$oxyalkylene in which the alkylene chain is linked to the group COORf or alternatively A is nothing; or a group —B—P(O)($OR_x$)($OR_y$) in which B takes one of the meanings given for A above and $R_x$ and $R_y$ independently take one of the meanings given for $R_f$ above;

W represents —G—$COORg$ in which G represents $(C_1-C_7)$ alkylene, $(C_2-C_7)$alkenylene, $(C_1-C_7)$oxyalkylene in which the alkylene chain is linked to the group $COOR_g$ or alternatively G is nothing, and $R_g$ represents a hydrogen atom or a $(C_1-C_7)$alkyl group; or alternatively W represents —D—P(O)($OR_z$)($OR_t$) in which D takes one of the meanings given above for G and $R_z$ and $R_t$ independently take one of the meanings given above for $R_g$;

and the pharmaceutically acceptable salts thereof, it being understood that (i) when $R_2, R_3, R_5$ and $R_7$ represent a hydrogen atom; X and Y represent an oxygen atom; $R_4$ represents methyl; and $R_6$ represents a hydrogen atom or a methyl group, then $R_1$ and R, together with the carbon atom which bears them, do not form any of the following divalent radicals:

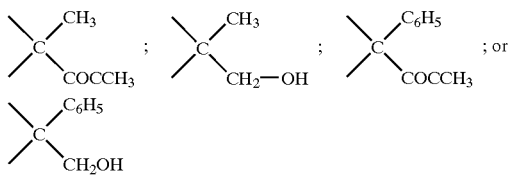

and (ii) when $R_4, R_5, R_6$ and $R_7$ represent a hydrogen atom; X and Y represent O; and R represents pyridyl, piperidyl or substituted piperidyl; then $R_1$ does not represent optionally substituted phenyl.

Formula I encompasses all the types of geometrical isomers and stereoisomers of the compounds of formula:

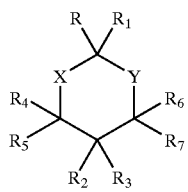

The physiologically acceptable salts of the compounds of formula (I) comprise the salts formed with metals and in particular with alkali metals, alkaline-earth metals and transition metals (such as sodium, potassium, calcium, magnesium or aluminum) or with bases such as aqueous ammonia or secondary or tertiary amines (such as diethylamine, triethylamine, piperidine, piperazine or morpholine) or with basic amino acids (such as lysine or arginine) or with osamines (such as meglumine) or with amino alcohols (such as 3-aminobutanol and 2-aminoethanol).

According to the invention, the term "alkyl" denotes a linear or branched hydrocarbon-based radical such as methyl, ethyl, propyl, isopropyl, butyl, tert-butyl, isobutyl, pentyl, hexyl or heptyl. When the alkyl group is substituted with one or more halogen atoms, it preferably represents perfluoroalkyl and in particular pentafluoroalkyl.

The term "alkoxy" denotes an alkyl group as defined above linked to an oxygen atom. Examples of this are the methoxy, ethoxy, isopropyloxy, butoxy and hexyloxy radicals.

The term "cycloalkyl" denotes saturated hydrocarbon-based groups which can be mono- or polycyclic and comprise from 3 to 12 carbon atoms, preferably from 3 to 8. The groups more particularly preferred are monocyclic cycloalkyl such as cyclopropyl, cyclobutyl, cyclopentyl, cyclohexyl, cycloheptyl, cyclooctyl, cyclononyl, cyclodecyl, cycloundecyl and cyclododecyl. The term "halogen" means a fluorine, chlorine, bromine or iodine atom.

The term "aryl" represents a mono- or bicyclic aromatic hydrocarbon-based group comprising 6 to 10 carbon atoms, such as phenyl or naphthyl.

The term "heterocycle" denotes a mono- or bicyclic ring of aromatic or non-aromatic nature comprising 3 to 10 ring members, 1 to 4 of which are occupied by identical or different hetero atoms chosen from oxygen, sulphur and nitrogen, such as, for example, aziridinyl, oxiranyl, oxazolyl, furyl, tetrahydrofuryl, benzothiazolyl, pyrimidinyl, pyridazinyl, piperidinyl, quinolyl, tetrahydroquinolyl, tetrazolyl, phthalazinyl, purinyl, indolyl, chromenyl, chromanyl, isochromanyl and pyrrolyl radicals.

The term "heterocycle" preferably denotes thienyl, furyl or pyrrolyl.

The phthalamido $(C_1-C_7)$alkyl group preferably denotes the radical of formula:

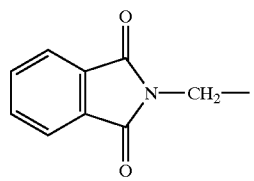

When R represents $(C_6-C_{10})$aryl, $(C_6-C_{10})$aryl$(C_1-C_7)$ alkyl or a heterocycle, the aryl group and the heterocycle can be substituted with a ($C_1$–$C_7$)alkylene chain. In this case, the two free valencies of the said alkylene chain are linked to two members of the aryl group, or of the heterocycle, respectively. Denoting the aryl group or the heterocycle as C, the structure formed can be represented in the following manner:

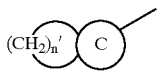

in which n' represents 1, 2, 3, 4, 5, 6 or 7.

When $R_1$ represents a group —CONR$_{10}$R$_{11}$ in which $R_{10}$ and $R_{11}$ together form a chain —(CH$_2$)$_r$—, $R_{10}$, $R_{11}$ and the nitrogen atom which bears them together form a 5- to 7-membered nitrogen ring comprising an endocyclic nitrogen atom.

When $R_2$ or $R_3$ represents fluorenyl, it is preferably the 9-fluorenyl group.

When $R_2$ and $R_3$ together form a —(CH$_2$)$_{r1}$— chain, $R_2$ and $R_3$ and the carbon atom which bears them together preferably form a cyclopropyl group.

The benzyl group may be mentioned as a preferred ($C_6$–$C_{10}$)aryl($C_1$–$C_7$)alkyl group.

When $R_2$ and $R_3$ together form the group (a):

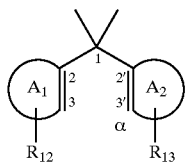

(a)

in which $A_1$, $A_2$, $R_{12}$ and $R_{13}$ are as defined above, $A_1$ and $A_2$ are hydrocarbon-based or heterocyclic rings comprising at least one ethylenic unsaturation >C═C< and bearing at least the radical $R_{12}$, or $R_{13}$, respectively, as substituent, but possibly bearing other substituents chosen from the radicals Z as defined above.

It is preferred for $A_1$ and $A_2$ to represent phenyl optionally substituted with one to four substituents Z.

It will be noted that the schematic representation of $A_1$ and $A_2$ given above means that $A_1$ and $A_2$ are linked to the same carbon atom (carbon 1) via carbon-carbon single bonds (bond 1-2, or 1-2', respectively), the carbon atom of the ring $A_1$, or of the ring $A_2$, respectively, engaged in this bond (2, or 2', respectively) being of sp$^2$ type, i.e. forming a double bond with a neighbouring carbon atom, located in an α position (carbon 3, or 3', respectively).

The substituent $R_{12}$ is located in any position on the ring $A_1$, and similarly $R_{13}$ is linked to the ring $A_2$ via any of the ring members of $A_2$. However, it is preferred for $R_{12}$ and $R_{13}$ to substitute, respectively, the sp$^2$ carbons in the α position, i.e. the carbons of type (3 and 3') as represented in the above scheme.

According to the invention, preferred meanings of the group (a) are:

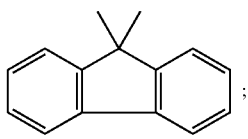

-continued

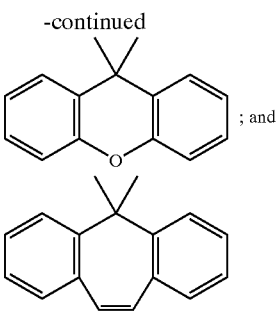

; and

The term "acyl" means a ($C_1$–$C_7$)alkylcarbonyl radical and the term "acylthio" means a ($C_1$–$C_7$)alkylthiocarbonyl radical of formula:

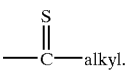

According to the invention, the term "alkenylene" radical moreover means a divalent hydrocarbon-based radical bearing one or more ethylenic double bonds, such as, for example, —CH═CH— or:

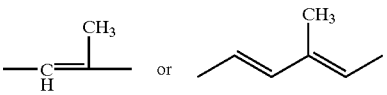

The "carbamoyl" radical denotes the monovalent radical of formula —CO—NH$_2$. The "($C_1$–$C_7$)alkylcarbamoyl" radical denotes a carbamoyl radical substituted with a $C_1$–$C_7$ alkyl group on the nitrogen atom, and the "di($C_1$–$C_7$)alkylcarbamoyl" radical denotes a carbamoyl radical substituted on the nitrogen atom with two $C_1$–$C_7$ alkyl groups.

The "($C_1$–$C_7$)alkylamino" radical denotes an amino group substituted on the nitrogen atom with a ($C_1$–$C_7$)alkyl radical and the "di($C_1$–$C_7$)alkylamino" radical denotes an amino group substituted on the nitrogen atom with two ($C_1$–$C_7$) alkyl radicals.

U.S. Pat. No. 4,056,540 describes compounds such as 4-phenyl-1,3-benzodioxane bearing a carboxylic function in position 2 of the benzodioxane ring, which have anticonvulsive or antiarrhythmic activity.

More recently, [4H]-1,3-benzodioxine-2-carboxylic acids and esters endowed with hypolipaemiant activity have been described in Eur. J. Med. Chem. Ther., 1983, 67.

However, the benzodioxane structure of these compounds differs entirely from the structure of the compounds of the invention.

Tetrahedron Asymmetry, vol. 3, No. 8, 1075–1086, 1992 describes the asymmetric synthesis of chiral ketals and in particular the synthesis of certain compounds of formula:

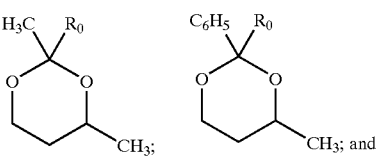

-continued

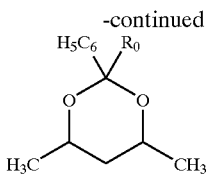

in which $R_0$ represents —COOCH$_3$ or —CH$_2$OH.

However, that document makes no reference at all to the pharmacological value of these compounds. In addition, J. Med. Chem., 1969, 51 describes anti-inflammatory compounds of 2-aryl-2-α-piperidyl-1,3-dioxane type. Among these compounds, those corresponding to one of the following formulae are relatively close to the compounds of the invention:

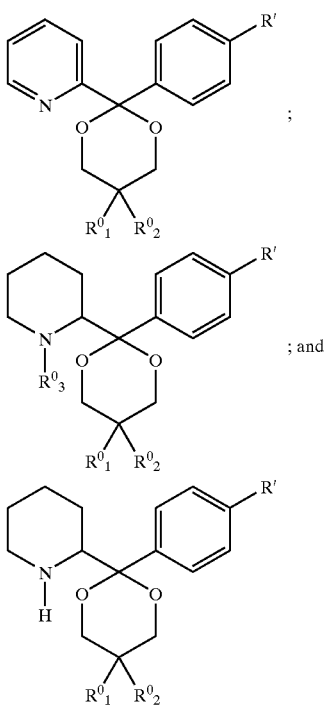

in which R' represents a hydrogen atom, a chlorine atom or a methoxy group; $R^0_1$ and $R^0_2$ represent either a hydrogen atom, an alkyl group or an aryl group; and $R^0_3$ is a methyl or methoxy group.

However, the anti-inflammatory activity of these compounds is in no way comparable with the hypolipidaemic and hypoglycaemic activity of the compounds of the invention.

Among the compounds of the invention, certain are preferred.

A first group of preferred compounds consists of the compounds of formula I as defined above for which X and Y represent an oxygen atom.

A second group of preferred compounds consists of the compounds of formula I in which $R_4$, $R_5$, $R_6$ and $R_7$ represent a hydrogen atom.

A third group of preferred compounds consists of the compounds of formula I in which:

R represents a hydrogen atom; a (C$_1$–C$_7$)alkyl group; a phthalamido (C$_1$–C$_7$)alkyl group; (C$_3$–C$_{12}$)cycloalkyl; a heterocycle as defined above for formula I; a (C$_6$–C$_{10}$)aryl group; or a (C$_6$–C$_{10}$)aryl(C$_1$–C$_7$)alkyl group; it being understood that the aryl groups present in R and the said heterocycle are optionally substituted with one or more substituents chosen from a (C$_1$–C$_7$) alkylene chain; a halogen atom; a phenyl group; (C$_1$–C$_7$)alkyl optionally substituted with one or more halogen atoms; (C$_1$–C$_7$)alkoxy; or a group —A—COORf in which A and Rf are as defined above for formula I;

$R_1$ represents a hydrogen atom; a (C$_1$–C$_7$)alkyl group; —(CH$_2$)$_t$—COORc in which t and Rc are as defined above for formula I;

$R_2$ and $R_3$ independently represent a hydrogen atom; a group (C$_6$–C$_{10}$)aryl or (C$_6$–C$_{10}$)aryl(C$_1$–C$_7$)alkyl; the aryl groups present in $R_2$ and $R_3$ optionally being substituted with one or more radicals chosen from a halogen atom; a (C$_1$–C$_7$)alkyl group optionally substituted with one or more halogen atoms; (C$_1$–C$_7$)alkoxy; N—(C$_1$–C$_7$)alkyl-carbamoyl; (C$_1$–C$_7$)alkylamino; nitro; cyano; and —A—COORf in which A and Rf are as defined above for formula I;

or alternatively $R_2$ and $R_3$ together form the group (a) as defined above for formula I in which $A_1$ and $A_2$ represent a phenyl group; and $R_{12}$ and $R_{13}$ together form a chain —(CH$_2$)$_m$—E—(CH$_2$)$_n$— in which m, n and E are as defined above for formula I, or a chain —CHR$_{14}$=CHR$_{15}$— in which $R_{14}$ and $R_{15}$ are as defined above for formula I;

or alternatively $R_2$ and $R_3$ together form a chain —(CH$_2$)$_{r1}$ in which $r_1$ is an integer equal to 2, 3, 4 or 5.

A fourth group of preferred compounds consists of the compounds of formula I in which R represents a hydrogen atom; a (C$_1$–C$_7$)alkyl group; (C$_3$–C$_{12}$)cycloalkyl; —(CH$_2$)$_p$—COOR$_b$ in which p and R$_b$ are as defined above for formula I; —(C$_6$–C$_{10}$) aryl or a heterocycle as defined above for formula I; it being understood that the said aryl group and the said heterocycle are optionally substituted with one or more substituents chosen from a halogen atom; a (C$_1$–C$_7$) alkyl group; (C$_1$–C$_7$)alkoxy; or —A—COORf in which A and Rf are as defined above for formula I;

$R_1$ represents a (C$_1$–C$_7$)alkyl or —(CH$_2$)$_t$—COOR$_c$ group in which t and R$_c$ are as defined above for formula I; a group —CONR$_{10}$R$_{11}$ in which $R_{10}$ and $R_{11}$ are as defined above for formula I;

$R_2$ and $R_3$ together form the group (a) as defined above for formula I in which $A_1$ and $A_2$ represent phenyl; and $R_{12}$ and $R_{13}$ together form a chain —(CH$_2$)$_m$—E—(CH$_2$)$_n$— in which m and n represent 0 and E represents a bond.

Among these compounds, those for which

R represents a hydrogen atom; (C$_1$–C$_4$)alkyl; —(CH$_2$)$_p$—COOR$_b$ in which p represents 1, 2 or 3 and R$_b$ represents a hydrogen atom or (C$_1$–C$_4$) alkyl; phenyl optionally substituted with a radical chosen from halogen, (C$_1$–C$_4$) alkyl, (C$_1$–C$_4$) alkoxy or —A—COORf in which A represents (C$_1$–C$_4$)alkylene or a bond and Rf represents H or (C$_1$–C$_4$)alkyl; furyl; thienyl; or pyrrolyl;

$R_1$ represents a (C$_1$–C$_4$)alkyl group; or alternatively —(CH$_2$)$_t$—COOR$_c$ in which t represents 0, 1, 2, 3 or 4 and R$_c$ represents a hydrogen atom or (C$_1$–C$_4$) alkyl;

$R_2$ and $R_3$ together form the group (a) as defined above for formula I, $A_1$ and $A_2$ representing phenyl and $R_{12}$ and $R_{13}$ together forming a bond or a (C$_1$–C$_4$)alkylene chain are particularly preferred.

A fifth group of preferred compounds consists of the compounds of formula I in which R represents $(C_6-C_{10})$aryl optionally substituted with a halogen atom;

$R_1$ represents —COOR$_c$ in which R$_c$ is as defined above for formula I;

$R_2$ and $R_3$ together form the group (a) as defined above for formula I in which $A_1$ and $A_2$ represent phenyl; and $R_{12}$ and $R_{13}$ together form a chain —(CH$_2$)$_m$—E—(CH$_2$)$_n$— in which m and n represent 0 and E represents a bond, O or S.

A sixth group of preferred compounds consists of the compounds of formula I in which R represents $(C_6-C_{10})$aryl optionally substituted with a halogen atom;

$R_1$ represents —COOR$_c$ in which R$_c$ is as defined above for formula I;

$R_2$ and $R_3$ together form the group (a) as defined above for formula I in which $A_1$ and $A_2$ represent phenyl; and $R_{12}$ and $R_{13}$ together form a chain —CHR$_{14}$=CHR$_{15}$— in which $R_{14}$ and $R_{15}$ are as defined above for formula I.

A seventh group of preferred compounds consists of the compounds of formula I for which at least one of the radicals R or $R_1$ bears a carboxylic group optionally in esterified form or in the form of amide. Among these compounds, the preferred ones are those for which R represents —(CH$_2$)$_p$—COOR$_b$ [lacuna] and R$_b$ are as defined above for formula I; or alternatively R represents $(C_6-C_{10})$aryl or $(C_6-C_{10})$aryl $(C_1-C_7)$ alkyl in which the aryl group present in R is substituted with a radical —A—COOR$_f$ in which A and R$_f$ are as defined above for formula I; or alternatively $R_1$ represents —(CH$_2$)$_t$—COOR$_c$ in which t and R$_c$ are as defined above for formula I; or alternatively $R_1$ represents $(C_6-C_{10})$aryl substituted with —G—COOR$_g$ in which G and R$_g$ are as defined above for formula I; or alternatively $R_1$ represents —CONR$_{10}$R$_{11}$ in which R$_{10}$ and R$_{11}$ are as defined above for formula I.

Among this seventh group of preferred compounds, those satisfying at least one of the following conditions are more particularly preferred:

X and Y represent an oxygen atom, $R_4$ to $R_7$ represent a hydrogen atom;

only one of the groups R or $R_1$ bears a carboxylic group which is optionally esterified or in the form of amide, the other being as defined for the third group of preferred compounds above; and $R_2$ and $R_3$ being as defined for the third group of preferred compounds;

only one of the groups R or $R_1$ bears a carboxylic group which is optionally esterified or in the form of amide, the other being as defined for the fourth group of preferred compounds above; and $R_2$ and $R_3$ being as defined for the fourth group of preferred compounds:

When R bears a carboxylic group optionally in ester form, it preferably represents phenyl substituted with —COOH; with —A—COOR$_f$ in which A represents $(C_2-C_5)$ alkenylene and R$_f$ represents H or $(C_1-C_4)$alkyl; or with $(C_1-C_4)$alkoxycarbonyl.

When $R_1$ bears a carboxylic group optionally in the form of ester or amide, it preferably represents —(CH$_2$)$_t$—COOR$_c$ in which t is 0, 1, 2, 3 or 4 and R$_c$ is H or $(C_1-C_4)$alkyl; or alternatively —CONR$_{10}$R$_{11}$ in which R$_{10}$ and R$_{11}$ are as defined above for formula I, but in which R$_{10}$ and R$_{11}$ do not together form a chain —(CH$_2$)$_r$—.

Examples of compounds of the invention are the following:

methyl 2-methyl-5,5-diphenyl[1,3]dioxane-2-carboxylate 2-methyl-5,5-diphenyl[1,3]dioxane-2-carboxylic acid ethyl 2-(4-chlorophenyl)-5,5-diphenyl[1,3]dioxane-2-carboxylate 2-(4-chlorophenyl)-5,5-diphenyl[1,3]dioxane-2-carboxylic acid ethyl 2-(4-methoxyphenyl)-5,5-diphenyl[1,3]dioxane-2-carboxylate 2-(4-methoxyphenyl)-5,5-diphenyl[1,3]dioxane-2-carboxylic acid ethyl 2-(4-methylphenyl)-5,5-diphenyl[1,3]dioxane-2-carboxylate 2-(4-methylphenyl)-5,5-diphenyl[1,3]dioxane-2-carboxylic acid ethyl 5,5-diphenyl-2-thiophen-2-yl[1,3]dioxane-2-carboxylate 5,5-diphenyl-2-thiophen-2-yl[1,3]dioxane-3-carboxylic acid ethyl 5,5-diphenyl[1,3]dioxane-2-carboxylate 5,5-diphenyl[1,3]dioxane-2-carboxylic acid ethyl 2,5,5-triphenyl[1,3]dioxane-2-carboxylate 2,5,5-triphenyl[1,3]dioxane-2-carboxylic acid ethyl 2-(4-fluorophenyl)-5,5-diphenyl[1,3]dioxane-2-carboxylate 2-(4-fluorophenyl)-5,5-diphenyl[1,3]dioxane-2-carboxylic acid ethyl 5,5-diphenyl-2-(5,5,8,8-tetramethyl-5,6,7,8-tetrahydro-2-naphthyl)-[1,3]dioxane-2-carboxylate ethyl 2-furan-2-yl-5,5-diphenyl[1,3]dioxane-2-carboxylate ethyl 2-(3-chlorophenyl)-5,5-diphenyl[1,3]dioxane-2-carboxylate 2-(3-chlorophenyl)-5,5-diphenyl[1,3]dioxane-2-carboxylic acid ethyl 2-isopropyl-5,5-diphenyl[1,3]dioxane-2-carboxylate ethyl 2-phenethyl-5,5-diphenyl[1,3]dioxane-2-carboxylate 2-phenethyl-5,5-diphenyl[1,3]dioxane-2-carboxylic acid ethyl 2-biphenyl-4-yl-5,5-diphenyl[1,3]dioxane-2-carboxylate ethyl 2-(3,4-dichlorophenyl)-5,5-diphenyl[1,3]dioxane-2-carboxylate 2-(3,4-dichlorophenyl)-5,5-diphenyl[1,3]dioxane-2-carboxylic [lacuna] 2-biphenyl-4-yl-5,5-diphenyl[1,3]dioxane-2-carboxylic acid ethyl 2-[2-(4-chlorophenyl)-5,5-diphenyl[1,3]dioxan-2-yl]acetate 2-[2-(4-chlorophenyl)-5,5-diphenyl[1,3]dioxan-2-yl]acetic acid ethyl 2-cyclohexyl-5,5-diphenyl[1,3]dioxane-2-carboxylate ethyl 2-(5,5-diphenyl[1,3]dioxan-2-yl)benzoate 2-(5,5-diphenyl[1,3]dioxan-2-yl)benzoic acid 5,5-diphenyl-2-(5,5,8,8-tetramethyl-5,6,7,8-tetrahydro-2-naphthyl)-[1,3]dioxane-2-carboxylic acid 2-furan-2-yl-5,5-diphenyl[1,3]dioxane-2-carboxylic acid 2-(1-naphthyl)-5,5-diphenyl[1,3]dioxane-2-carboxylic acid 2-(1-naphthyl)-5,5-diphenyl[1,3]dioxane-2-carboxylic acid 2-isopropyl-5,5-diphenyl[1,3]dioxane-2-carboxylic acid [2-(4-chlorophenyl)-5,5-diphenyl[1,3]dioxan-2-yl]methanol 2-cyclohexyl-5,5-diphenyl[1,3]dioxane-2-carboxylic acid [2-(4-chlorophenyl)-5,5-diphenyl[1,3]dioxan-2-yl]1-piperidyl ketone 2-[(2-methyl-5,5-diphenyl[1,3]dioxan-2-yl)methyl]isoindole-1,3-dione ethyl 5-[4-(5,5-diphenyl[1,3]dioxan-2-yl)phenyl]-3-methylpenta-2,4-dienoate 5-[4-(5,5-diphenyl[1,3]dioxan-2-yl)phenyl]-3-methylpenta-2,4-dienoic acid 2-(ethoxycarbonylmethylaminocarbonyl)-2-(4-chlorophenyl)-5,5-diphenyl[1,3]dioxane 2-carboxymethylaminocarbonyl-2-(4-chlorophenyl)-5,5-diphenyl[1,3]dioxane ethyl 5,5-diphenyl-2-(4-trifluoromethylphenyl)-[1,3]dioxane-2-carboxylate 2-[4-(5,5-diphenyl[1,3]dioxan-2-yl)phenoxy]-2-methylpropionic acid 2-(4-trifluoromethylphenyl)-5,5-diphenyl[1,3]dioxan-2-ylcarboxylic acid ethyl 2,5,5-tris(4-chlorophenyl)-[1,3]dioxane-2-carboxylate 2,5,5-tris(4-chlorophenyl)-[1,3]dioxane-2-carboxylic acid ethyl 2-(4-chlorophenyl)-5,5-bis(4-fluorophenyl)-[1,3]dioxane-2-carboxylate 2-(4-chlorophenyl)-5,5-bis(4-fluorophenyl)-[1,3]dioxane-2-carboxylic acid ethyl 2-(4-chlorophenyl)-5,5-bis(3-trifluoromethyl-phenyl)-

[1,3]dioxane-2-carboxylate 2-(4-chlorophenyl)-5,5-bis (3-trifluoromethylphenyl)-[1,3]dioxane-2-carboxylic acid ethyl 2-(4-chlorophenyl)spiro[[1,3]dioxane-5,5'-5'H-dibenzo[a,d]cycloheptene]-2-carboxylate 2-(4-chlorophenyl)spiro[[1,3]dioxane-5,5'-5'H-dibenzo[a,d] cycloheptene]-2-carboxylic acid 2-(4-chlorophenyl) spiro[[1,3]dioxane-5,9'-xanthene]-2-carboxylic acid 2-(4-chlorophenyl)spiro[1,3-dioxane-5,9'-xanthene]-2-carboxylic acid ethyl 2-(4-chlorophenyl)-5-(9H-fluoren-9-yl)-[1,3]dioxane-2-carboxylate ethyl 2'-(4-chlorophenyl)spiro[cyclobutane-1,5'-[1,3]dioxane]-2'-carboxylate 2-(4-chlorophenyl)spiro[cyclobutane-1,5'-[1,3]dioxane]-2'-carboxylic acid 5,5-dibenzyl-2-(4-chlorophenyl)-[1,3]dioxane-2-carboxylic acid methyl 2-methylspiro[[1,3]dioxane-5,9'-fluorene]-2-carboxylate 2-methylspiro[[1,3]dioxane-5,9'-fluorene]-2-carboxylic acid ethyl 2-(2-methylspiro[[1,3]dioxane-5,9'-fluoren]-2-yl)acetate 2-(2-methylspiro[[1,3] dioxane-5,9-fluoren]-2-yl)acetic acid methyl 2-(2-methoxycarbonylethylspiro[[1,3]dioxane-5,9'-fluoren]-2-yl)acetate 2-(2-carboxyethylspiro[[1,3] dioxane-5,9'-fluoren]-2-yl)acetic acid methyl 4-(2-methylspiro[[1,3]dioxane-5,9'-fluoren]-2-yl)benzoate butyl spiro[[1,3]dioxane-5,9'-fluorene]-2-carboxylate spiro[[1,3]dioxane-5,9'-fluorene]-2-carboxylic acid methyl 2-phenylspiro[[1,3]dioxane-5,9'-fluorene]-2-carboxylate 2-phenylspiro[[1,3]dioxane-5,9'-fluorene]-2-carboxylic acid ethyl 2-[4-methylphenyl]spiro[[1,3]dioxane-5,9'-fluorene]-2-carboxylate ethyl 2-[4-methoxyphenyl]spiro[[1,3]dioxane-5,9'-fluorene]-2-carboxylate 2-[4-methoxyphenyl]spiro[[1,3]dioxane-5,9'-fluorene]-2-carboxylic acid ethyl 2-[4-chlorophenyl] spiro[[1,3]dioxane-5,9'-fluorene]-2-carboxylate 2-[4-chlorophenyl]spiro[[1,3]dioxane-5,9'-fluorene]-2-carboxylic acid ethyl 2-[2-thienyl]spiro[[1,3]dioxane-5,9'-fluorene]-2-carboxylate 2-[2-thienyl]spiro[[1,3] dioxane-5,9'-fluorene]-2-carboxylic acid 2-(4-chlorophenyl)-5,5-diphenyl[1,3]oxazinane Among these compounds, the following are particularly preferred:

ethyl 2-(4-chlorophenyl)-5,5-diphenyl[1,3]dioxane-2-carboxylate 2-(4-chlorophenyl)-5,5-diphenyl[1,3] dioxane-2-carboxylic acid ethyl 2,5,5-tris(4-chlorophenyl)-[1,3]dioxane-2-carboxylate 2,5,5-tris(4-chlorophenyl)-[1,3]dioxane-2-carboxylic acid ethyl 2-(4-chlorophenyl)spiro[[1,3]dioxane-5,9'-fluorene]-2-carboxylate 2-(4-chlorophenyl)spiro[[1,3]dioxane-5,9'-fluorene]-2-carboxylic acid.

The compounds of the invention and those defined in points (i) and (ii) above can be prepared using any of the following processes.

In general, the compounds of formula I can be prepared by reaction of a compound of formula:

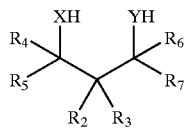

in which X, Y and $R_2$ to $R_7$ are as defined above for formula I, it being understood that X or Y can also represent a nitrogen atom substituted with a function which is a precursor of the radical $R_a$, with a ketone of formula III:

in which R and $R_1$ are as defined above for formula I.

When, in formula I, X and Y are an oxygen atom, the processes A, B, C or D can be used.

Process A:

A diol of formula II

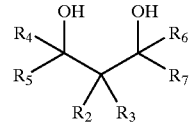

in which $R_2$ to $R_7$ are as defined for formula I, is reacted with a carbonyl derivative of formula III:

in which R and $R_1$ are as defined above for formula I, to give a compound of formula I in which X and Y represent an oxygen atom.

The reaction used is a cyclization reaction. This reaction is carried out under the standard conditions, either in the presence of a specific catalyst as described in:

S. Fukusawa et al., Synlett, 1995, 1077.

G. C. G. Pals, J. Chem. Research, 1996, 426.

B. P. Bandgar, Synth. Commun., 1997, 27(4), 627.

K. Ishihara, Synlett, 1987, 839.

S. B. Lee, Synthesis, 1991, 368 or in the absence of a catalyst, as described in F. A. J. Meskens, Synthesis, 1981, 501.

H. Suemune et al., Chem. Pharm. Bull., 1990, 38(11), 3155.

The reaction is typically carried out in an aprotic solvent which forms an azeotrope with water, such as toluene, at a temperature of from 50 to 150° C., better still from 90 to 120° C., in the presence of an excess of compound III. The molar ratio of compound III to the diol II will preferably be between 1.1 and 2, for example between 1.3 and 1.7.

In order to increase the yields, it is recommended to react the diol with the carbonyl compound in the presence of an acid catalyst such as para-toluenesulphonic acid, while removing the water from the reaction medium.

By way of example, the diol II may be reacted with the carbonyl derivative III in the presence of 0.2 equivalent of para-toluenesulphonic acid at the reflux point of toluene in Dean-Stark apparatus for 6 to 8 hours.

As a variant, the reaction can be carried out in a halogenated aliphatic hydrocarbon at a temperature of between 15 and 30° C. in the presence of a Lewis acid. In this case, it is preferable for the molar ratio of the diol II to the carbonyl derivative III to range between 1.5 and 3, better still between 1.8 and 2.2.

By way of example, the diol II may be reacted with two equivalents of the derivative III in methylene chloride in the presence of one equivalent of $BF_3$-etherate at room temperature for 12 to 48 hours.

Process B:

The compounds of formula I in which X and Y represent an oxygen atom can be prepared by reacting an alkali metal or alkaline-earth metal salt of a diol of formula II:

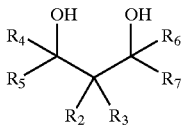

in which $R_2$ to $R_7$ are as defined for I above, with a dihalo compound of formula IV:

in which R and $R_1$ are as defined for I above and X represents a halogen atom.

The metal salt of the diol II used as reagent is a salt in which the two hydroxyl functions are salified, either with the same metal cation $M^{2+}$ of an alkaline-earth metal, or with two cations $M^+$ of an alkali metal. It is preferred to carry out this reaction starting with an alkali metal salt and in particular the sodium salt.

According to a preferred embodiment of the invention, the metal salt is formed in situ in the reaction medium by the action of a metal hydride (and for example a sodium hydride) on the diol of formula II.

The reaction of the salt of the diol II with compound IV is preferably carried out in a polar aprotic solvent, such as an ether, at a temperature of between 15 and 30° C., preferably in a slight excess of the metal salt of the diol II.

In order to increase the yields, the process will be performed, for example, in the presence of a crown ether as taught in Eur. J. Med. Chem. Chim. Ther. 1983, 67.

By way of example, 1.1 to 1.5 equivalents of the diol II are reacted with compound IV in which X represents chlorine, in anhydrous dioxane as solvent, in the presence of sodium hydride and 18-crown-6 at room temperature (20° C.).

Process C:

The compounds of formula I in which X and Y represent an oxygen atom can also be obtained by transacetalization reaction, and more specifically by reacting the diol of formula II:

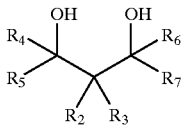

in which $R_2$ to $R_7$ are as defined above for formula I, with a ketal of formula V:

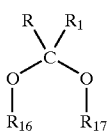

in which R and $R_1$ are as defined above for formula I and $R_{16}$ and $R_{17}$ independently represent ($C_1$–$C_7$)alkyl or together form an alkylene chain of —$(CH_2)_{r'}$— type in which r' is an integer equal to 4, 5 or 6.

This reaction is preferably carried out in an aprotic solvent which forms an azeotrope with water, such as toluene, at a temperature of between 80 and 150° C., for example at a temperature of between 90 and 120° C. In order to increase the yields, it is desirable to perform the process in the presence of an excess of the diol of formula II (1.5 to 3 equivalents, preferably 1.8 to 2.2 equivalents) and of an acid catalyst, such as para-toluenesulphonic acid.

Inspiration may be taken from J. Am. Chem. Soc. 1958, 80, 6613.

By way of example, two equivalents of the diol II are reacted with one equivalent of compound V in the presence of 0.2 equivalent of para-toluenesulphonic acid in toluene maintained at reflux in Dean-Stark apparatus for 1 to 4 hours.

Process D:

The compounds of formula I in which X and Y represent an oxygen atom can be synthesized from the diols of formula II by forming the intermediate silyl derivatives according to reaction scheme 3 below:

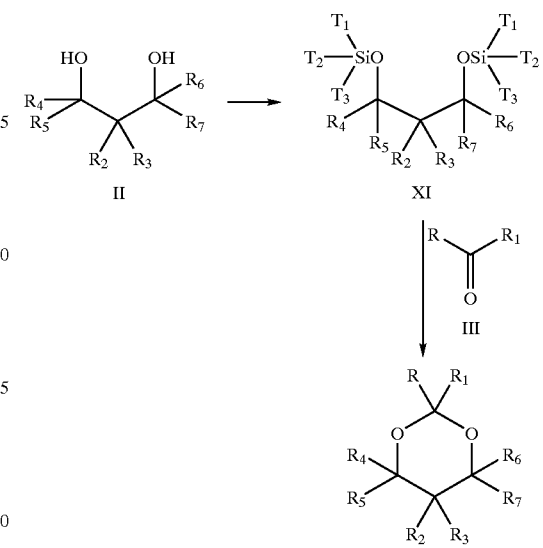

Scheme 3

In this scheme, R and $R_1$ to $R_7$ are as defined for formula I and $T_1$ to $T_3$ independently represent ($C_1$–$C_4$) alkyl.

According to this process, the disilyl derivative XI is prepared in a conventional manner. To do this, a person skilled in the art will refer, for example, to Tetrahedron 1994, 50, 42, 12143 and Chem. Lett. 1994, 263. The disilyl derivative XI is preferably formed in situ in the presence of the ketone III with which it reacts as it is formed. These two reactions are, in this case, preferably carried out in a polar aprotic solvent such as a halogenated aliphatic hydrocarbon. The molar ratio of the ketone III to the diol II is preferably between 1.1 and 2, better still between 1.3 and 1.7. The silylation is carried out, for example, by the action of an alkoxytrialkylsilane derivative (in which the alkyl parts are $C_1$–$C_6$). Preferably, a large excess of alkoxytrialkylsilane is reacted with the diol II in the presence of trifluoromethanesulphonate as catalyst. The molar ratio of the alkoxytrialkylsilane to the diol is, for example, between 2 and 6, better still between 3 and 5.

The temperature of the reaction medium is usually maintained between −40 and −10° C.

By way of example, 1 equivalent of the ketone of [sic] III can be reacted with 1.3 equivalents of the diol II in anhydrous methylene chloride in the presence of 4 equivalents of isopropoxytrimethylsilane at temperatures of about −20° C. and in the presence of 0.01 equivalent of trimethylsilyl trifluoromethane-sulphonate. The reaction time is typically about 3 hours.

The compounds of formulae III, IV and V are commercially available or easily prepared from active compounds by carrying out standard methods of organic chemistry.

For the synthesis of the acetals of formula V, a person skilled in the art may also refer to Synthesis 1983, 203.

Certain diols of formula II are described in the literature.

The diols of formula II can be obtained by carrying out any of the processes a), b) or c) below.

Process a).

The reaction scheme is represented below

Scheme 4

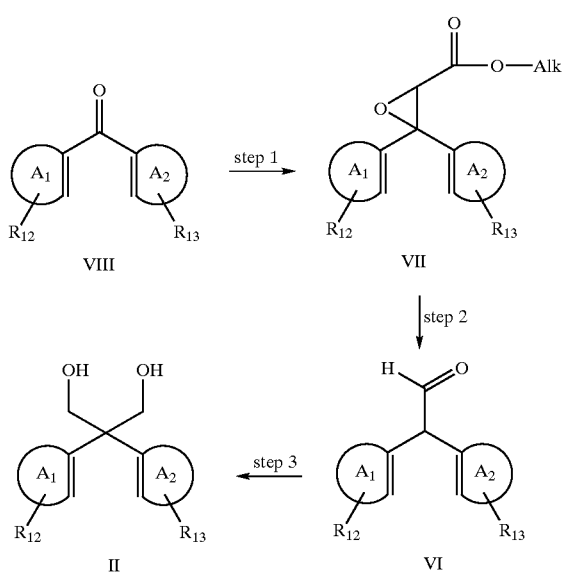

In this scheme, $A_1$, $A_2$, $R_{12}$ and $R_{13}$ are as defined for formula I and Alk represents $(C_1-C_6)$alkyl.

To synthesize the epoxide VII from the ketone VIII, a person skilled in the art may be inspired by the research described in:

J. Am. Chem. Soc. 1958, 80, 6389 or J. Am. Chem. Soc. 1931, 53, 205.

The ketone of formula VIII may, for example, be reacted with a compound of formula IX:

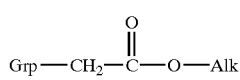

in which Grp represents a leaving group (such as a chlorine atom) and Alk represents $(C_1-C_6)$alkyl in the presence of a base such as an alkali metal hydride or an alkali metal alkoxide. The reaction is preferably carried out in a polar aprotic solvent, such as an ether, at a temperature not exceeding 45° C. Since the reaction is exothermic in certain cases, the reaction medium should be cooed during the reaction. An excess of the compound IX relative to the compound VIII will advantageously be used. A molar ratio of compound IX to compound VIII of between 1.2 and 2 is appropriate.

By way of example, compound VIII will be reacted with 1.5 equivalents of ethyl chloroacetate in the presence of sodium hydride or sodium ethoxide in tetrahydrofuran, the reaction medium being maintained at a temperature below 45° C.

The aldehyde of formula VI is obtained from the epoxide VII in a conventional manner. Reference may be made, for example, to J. Med. Chem. 1968, 11, 380.

In general, the epoxide of formula VII is treated, in step 2, with a base such as potassium hydroxide at a temperature of between 15 and 120° C. For example, when Alk represents ethyl, the epoxide VII is refluxed in the presence of KOH for 8 hours.

In order to convert the aldehyde obtained of formula VI into the diol of formula II, the process will be performed as indicated in J. Med. 1969, 12, 462 and J. Am. Chem. Soc. 1949, 2031.

By way of example, the diol II is obtained by treating the aldehyde VI with formaldehyde in aqueous solution (from 1.2 to 2 equivalents of formaldehyde) in the presence of a base such as potassium carbonate (from 1 to 2 equivalents). The reaction temperature is advantageously between 15 and 130° C., preferably between 80 and 120° C.

The ketones of formula VIII are commercially available or readily prepared from commercial compounds.

Process b):

Another way of performing the process is illustrated in scheme 5 below.

Scheme 5

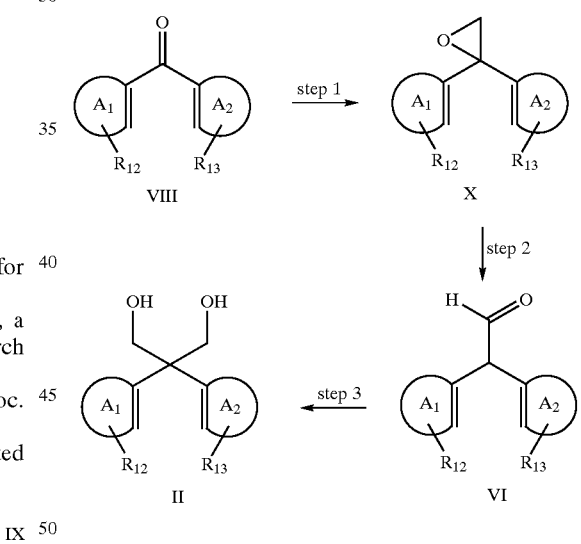

Starting with the ketone VIII, the aldehyde VI is prepared by forming the intermediate epoxide X by carrying out a process similar to the one illustrated in J. Org. Chem. 1972, 35, 25, 4075. In order to convert the aldehyde VI into the diol of formula II, the process is performed as described above for process a). Typically, the aldehyde VI is reacted in ethanol with, for example, 0.2 mol of aqueous 37% formaldehyde solution in the presence of a base which can be potassium carbonate (0.05 mol) at reflux for 20 hours. An amount of water representing about ⅕ of that of ethanol will advantageously be added to the medium.

Process c):

According to a third variant, the diol of formula II can be obtained according to reaction scheme 6 below, in which Alk represents $(C_1-C_6)$alkyl and $A_1$, $A_2$, $R_{12}$ and $R_{13}$ are as defined above for formula I:

Scheme 6

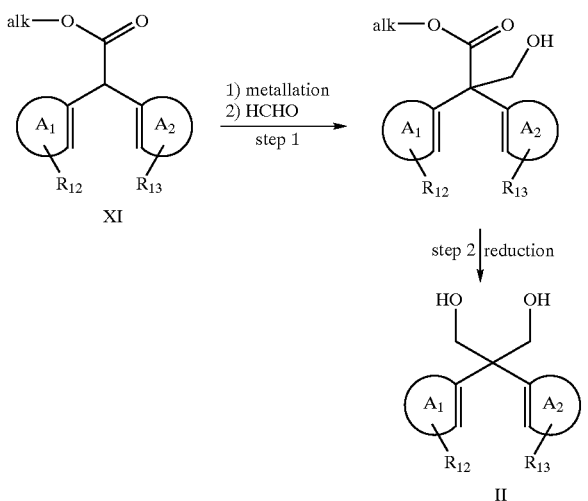

The ester XI can be metallated by the action of butyllithium in tetrahydrofuran at a temperature of between −70 and −30° C. The reaction mixture is then treated with gaseous formaldehyde at a temperature of from 0 to 25° C., which gives the α-hydroxymethyl derivative. This compound is reduced by the action of a suitable reducing agent, in a conventional manner. Lithium aluminum hydride may be mentioned as a reducing agent. In this case, the reduction is complete after two hours, the reaction medium being maintained at a temperature below 10° C.

Certain compounds of formula II are novel. According to one of its aspects, the invention relates to the diols of formula II chosen from:

2,2-bis(4-fluorophenyl)propane-1,3-diol;

2,2-bis(3-trifluoromethylphenyl)propane-1,3-diol;

5-hydroxymethyl-5H-dibenzo[a,d]cyclohepten-5-ylmethanol; and (9-hydroxymethyl-9H-xanthen-9-yl)methanol which are novel.

The esters of formula XI are commercial products or are readily prepared from commercial products.

Process E below allows the formation of the compounds of formula I in which X represents O and Y represents S.

Process E

According to this process, a compound of formula XII:

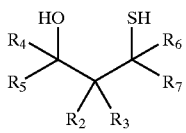

in which $R_2$ to $R_7$ are as defined above for formula I, is reacted with the ketone of formula III

This reaction may be carried out by analogy with the processes described in the following publications, which also illustrate the preparation of the compounds of formula XII:

E. L. Eliel et al., J. Am. Chem. Soc., 1962, 84, 2377

A. J. Liepa et al., Aust. J. Chem., 1986, 39, 1747

R. Caputo et al., Synthesis, 1987, 386

B. Burczyk et al., Synthesis, 1982, 831

F. E. Ziegler et al., Tetrahedron Lett., 1978, 31, 2767

A technique based on the one described in Caputo et al., Synthesis, 1987, 386 consists in reacting the ketone III with the compound XII in the presence of polystyryldiphenyliodophosphonium iodide in a polar aprotic solvent such as acetonitrile, at a temperature of between 10 and 40° C., preferably at room temperature (about 20° C. ). Using anhydrous acetonitrile at 20° C., the reaction is complete within 30 minutes to 2 hours.

For the synthesis of the compounds of formula I in which X and Y are a group —$NR_a$—, process F below may be used.

Process F

According to this process, the diamine XIII:

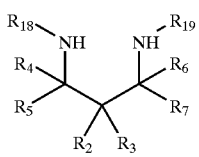

in which $R_2$ to $R_7$ are as defined for formula I and $R_{18}$ and $R_{19}$ independently have one of the meanings given for $R_a$ in formula I or represent a precursor radical leading to any of these meanings, is reacted with the ketone of formula III:

The operating conditions for carrying out this reaction will be readily determined by a person skilled in the art, who may perform the process, for example, as taught in:

P. M. Hardy et al., J. Chem. Soc., Perkin Trans. 1, 1977, 1954

T. Araki et al., Macromolecules, 1995, 21(7), 1988

Carpentier et al., Tetrahedron, 1985, 41(18), 3803

R. Gosmini et al., Synlett, 1991, 111

A. Alexakis et al., Synlett, 1991, 625

M. Gray et al., Synlett, 1991, 729

T. Okawara et al., J. Chem. Soc., Chem. Commun., 1990, 20, 1385

Typically, the reaction of XIII with III is carried out in an aprotic solvent such as an aromatic hydrocarbon at a temperature of from 80 to 150° C., preferably from 90 to 120° C.

The molar ratio of III to XIII may be between 1 and 5, better still between 1 and 3. In order to increase the reaction kinetics and the yield, this reaction can advantageously be carried out in the presence of an acid catalyst, such as para-toluenesulphonic acid.

By way of example, one equivalent of XIII is reacted with 1 to 3 equivalents of the ketone III in refluxing toluene in the presence of from 0.2 to 2.2 equivalents of para-toluenesulphonic acid in Dean-Stark apparatus for 6 to 24 hours.

When $R_{18}$ or $R_{19}$ represents a radical which is a precursor of $R_a$, the reaction of XIII with III will be followed by a step of converting the resulting compound into the compound of formula I.

The operating conditions for this conversion will be readily determined by a person skilled in the art using his or her general knowledge.

The compounds of XIII type can be synthesized, for example, according to the schemes described in H. P. Kaufmann et al., Chem. Ber., 1959, 2810.

For the synthesis of the compounds of formula I in which X represents C and Y represents —NR$_a$—, process G below may be carried out.

Process G

Compound XIV below:

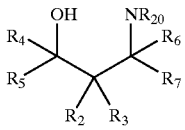

XIV in which R$_2$ to R$_7$ are as defined for I and R$_{20}$ has one of the meanings given for R$_{17}$ above, is reacted with the ketone of formula III: RCO—R$_1$ in which R and R$_1$ are as defined for formula I.

The compounds of formula I in which R$_a$ is other than H can be obtained from the corresponding compounds of formula I in which R$_a$ is H by N-alkylation. The N-alkylation will be carried out in a manner which is known per se to those skilled in the art, for example by the action of an alkyl iodide or a dialkyl sulphate.

The operating conditions for the reaction of compound XIV with the ketone III are those conventionally used in the technique for this type of reaction. They may be derived from any of the following publications:

W. Schneider et al., Arch. Pharm. Ber. Dtsch. Pharm. Ges., 1966, 299, 997

G. Bernath et al., Pharmazie, 1983, 38, 2, 89

E. D. Bergmann et al., J. Chem. Soc., 1963, 3736

E. Biekert et al., Chem. Ber., 1961, 1664

In general, the operating conditions prescribed in the case of process F may be suitable.

By way of example, the amino alcohol XIV can be reacted with 1 to 3 equivalents of the ketone III in refluxing toluene in the presence of from 0.2 to 1.2 equivalents of para-toluenesulphonic acid in Dean-Stark apparatus for 4 to 10 hours.

The amino alcohols XIV can be prepared, for example, according to the schemes described in C. A. Grob et al., Helv. Chem. Acta, 1972, 501.

The publications cited above also illustrate the preparation of the amino alcohols of formula XIV.

The compounds of formula I in which X and Y represent S may be prepared by carrying out process H below.

Process H:

According to this process, the dithiol of formula XV:

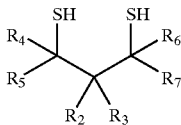

XV in which R$_2$ to R$_7$ are as defined for formula I, is reacted with the ketone of formula III: RCO—R$_1$ in which R and R$_1$ are as defined above for I.

The process will preferably be performed in a polar aprotic solvent such as an ether at a temperature of from 15 to 30° C., better still from 18 to 25° C., in the presence of a slight excess of the ketone III.

The molar ratio of compound XV to compound III is usually between 1 and 2, preferably between 1.3 and 1.7.

More generally, reference may be made to

I. Shahak et al., J. Chem. Soc. 1966, 1005

G. A. Olah et al., Synthesis, 1981, 282 for the implementation of this reaction.

By way of example, compound XV is reacted with 1.2 equivalents of the ketone III in dioxane at 20° C. until the reaction is complete (from 5 minutes to 2 hours are generally sufficient).

The dithiols of formula XV are prepared in a manner which is known per se and exemplified in particular in J. Houk et al., J. Amer. Chem. Soc. 1987, 6825–6836 and E. L. Eliet et al., J. Amer. Chem. Soc., 1976, 3583–3590.

The hypolipidaemic and hypoglycaemic activity of the compounds of the invention result from their capacity to activate the PPARα and PPARγ type receptors. The activation of the PPARα receptors has been illustrated using rat primary hepatocytes in the case of the compound of Example 4.

More specifically, the effects of the compounds of the invention on the expression of genes involved in lipid metabolism (Acyl CoA oxidase) or lipid transport (apo A-I, apo C-III) were studied in the model of rat hepatocytes in primary culture obtained according to a modification of the initial procedure of Berry and Friend (Berry M, Friend D. 1969. J. Cell. Biol. 43: 506–520) described previously (Berthou L, Saladin R, YaQoob P, Branellec D, Calder P, Fruchart J C, Denèfle P, Auwerx J, Staels B. 1995. Eur. J. Biochem.: 232, 179–187). These genes are modulated in a coordinated manner by PPAR and thus represent good markers of the activation of the PPARα mainly expressed in the hepatic tissue (Braissant O, Foufelle F, Scotto C, Dauca M, Wahli W; 1995. Endocrinology: 137, 354–366). The hepatocytes were isolated by "in situ" hepatic infusion of collagenase (Wistar rats whose weight ranges between 200 and 250 g), homogenization of the tissue, filtration through Nylon, centrifugation at low speed and inoculation at a rate of $10^7$ cells per dish (if the viability estimated by the Trypan blue test exceeds 90%). The cells were stimulated from the start of inoculation (compounds dissolved in DMSO) in L15 culture medium supplemented with 10% foetal calf serum, 0.2% (mass/volume) of bovine serum albumin (BSA), 3 g/l of glucose and 26 mM bicarbonate, 2 mM glutamine and antibiotics. After incubation for 24 hours at 37° C. in a humid atmosphere of 5% CO$_2$/95% air, the cells were lysed in guanidine thiocyanate solution, the RNAs extracted with phenol (pH4/chloroform, assayed by spectrophotometer, transferred onto a membrane (Dot blot, Northern blot) and hybridized with specific molecular probes according to the procedures described previously (Staels B, Van Tol A, Andreu T, Auwerx J; 1992. Atherioscler. Thromb. 12: 286–294). The cDNA of the clone 36B4 coding for the human PO acidic ribosomal phosphoprotein (Masiakowski P, Breathnach R, Bloch J, Gannon F, Krust A, Chambon P; 1982. Nucl. Acids Res. 10: 7895–7903), whose tissue expression is stable, was used as control probe.

The cDNA probes were labelled with $^{32}P$ using random primers by means of the kit sold by Boehringer Mannheim. The membranes were hybridized with 1.5×10$^6$ cpm/ml of each probe according to the procedure described previously (Staels B, Van Tol A, Andreu T, Auwerx J; 1992. Atherioscler. Thromb. 12: 286–294). They were washed once in 0.5×SSC buffer and 0.1% SDS at room temperature for 10 min and twice in the same buffer at 65° C. for 30 min, and then autoradiographed (X-OMAT-AR film, Kodak). The autoradiographs were analysed by densitometry (Biorad GS670 densitometer).

The effects of the compound of Example 4 on the hepatic gene expression were studied.

The hepatic expression of the ACO gene is increased by a 24-hour treatment with the compound of Example 4 (25

μM). This response is typical of the effects observed previously (Berthou L, Saladin R, YaQoob P, Branellec D, Calder P, Fruchart J C, Denèfle P, Auwerx J, Staels B. 1995. Eur. J. Biochem.: 232, 179–187) (Staels B, Vu-Dac N, Kosykh V. A., Saladin R, Fruchart J. C., Dallongeville J., Auwerx J.; 1995. J. Clin. Invest. 95: 705–712) when the hepatocytes are treated with fibrates which are AR$\alpha$ ligands and activators (Devchand P, Keller H, Peters J, Vasquez M, Gonzales F, Wahli W.; 1996. Nature; 384: 39–43). These results suggest that the compounds of the invention act via PPAR$\alpha$. Similar results were reproduced in two independent experiments.

Expression of the mRNAs coding for the ACO genes in rat hepatocytes in primary culture treated for 24 hours with the compound of Example 4 (25 μm).

The values are expressed relative to the base value (%).

|  | ACO |
| --- | --- |
| Control | 100 ± 0 |
| Compound of Example 4 | 427 ± 63 |

Activation of the PPAR$\gamma$ was similarly demonstrated in the case of the compound of Example 4.

Analysis of the activation of PPAR$\gamma$ is based on the transfection of a DNA allowing the expression of a reporter gene (CAT (chloramphenicol acetyltransferase)) under the control of PPAR in cells which express PPAR$\gamma$. The reporter plasmid J3TkCAT described previously (Fajas L, Auboeuf D, Raspé E, Schoonjans K, Lefebvre A. M., Saladin R, Najib J, Laville M, Fruchart J. C., Deeb S, Vidal-Puig A, Flier J. Briggs M, Staels B, Vidal H, Auwerx J.; 1997. J. Biol. Chem. 272: 18779–18789) comprises three copies of the PPAR response element for human apo A-II gene which are cloned upstream of the promoter for the thymidine kinase gene of the herpes simplex virus in the plasmid pBLCAT4 (Staels B, Vu-Dac N, Kosykh V. A., Saladin R, Fruchart J. C., Dallongeville J, Auwerx J.; 1995. J. Clin. Invest. 95: 705–712). The cells used are the green monkey CV1 cells and COS cells transformed by the SV40 virus and which express PPAR$\gamma$ (Forman B, Tontonoz P, Chen J, Brun R, Spiegelman B, Evans R.; 1995. Cell. 83: 803–812). These cells were inoculated at a rate of 300,000 cells per dish (dishes 5 cm in diameter) and transfected with 500 ng of reporter DNA according to a process described previously (Fajas L, Auboeuf D, Raspé E, Schoonjans K, Lefebvre A. M., Saladin R, Najib J. Laville M, Fruchart J. C., Deeb S, Vidal-Puig A, Flier J, Briggs M, Staels B, Vidal H, Auwerx J.; 1997. J. Biol. Chem. 272: 18779–18789). After 5 to 6 hours, the cells were washed twice with PBS and incubated for 36 hours in fresh culture medium (DMEM) containing 10% foetal calf serum. After transfection, the cells were lysed and the CAT activity was measured according to the procedure described previously (Fajas L, Auboeuf D, Raspé E, Schoonjans K, Lefebvre A. M., Saladin R, Najib J, Laville M, Fruchard J. C., Deeb S, Vidal-Puig A, Flier J, Briggs M, Staels B, Vidal H, Auwerx J.; 1997. J. Biol. Chem. 272: 18779–18789). It is expressed relative to the control value.

The effects of the compound of Example 4 are given in FIG. 1.

The activity of the CAT reporter gene of Cos cells transfected with the J3TkCAT construct is increased when these cells are incubated in the presence of the compound of Example 4. On the other hand, when the Cos cells are transfected with the pBLCAT4 plasmid lacking the PPAR response element, the compound of Example 4 is inactive.

In FIG. 1, T represents the control value for each reporter (TkCAT or J3TkCAT).

In a final test, the hypolipidaemic and hypoglycaemic activity of the compound of Example 4 was evaluated in db/db mice.

Two-month-old db/db mice were treated orally for 15 days with the compound of Example 4 (100 mg/kg/day). Each study group comprises seven animals. After three days (D3) and 15 days (D15) of treatment, retro-orbital samples were taken after light anaesthesia and without fasting.

The following measurements were taken:

assay of the glycaemia (glucose oxidase) at D3 and D15 and of the lipid parameters on the sera at D15 (COBAS): triglycerides, total cholesterol (CHOL), HDL cholesterol (HDL-C) and free fatty acids (FFA) (assay kit from BioMérieux and Wako Chemicals).

The results obtained are given in the table below. The measurements given in this table are average values±standard error.

|  | Control | Example 4 | % variation relative to the control |
| --- | --- | --- | --- |
| Glycaemia D3 (mM) | 33.19 ± 6.33 | 21.35 ± 5.67* | −36 |
| Glycaemia D15 (mM) | 39.19 ± 9.21 | 29.90 ± 10.22* | −24 |
| Triglycerides D15 (mM) | 1.78 ± 0.54 | 1.07 ± 0.74* | −40 |
| CHOL D15 (mM) | 2.69 ± 0.36 | 2.60 ± 0.13 | −3 |
| HDL-C D15 (mM) | 1.65 ± 0.32 | 1.64 ± 0.19 | −1 |
| FFA D15 (mM) | 0.72 ± 0.20 | 0.52 ± 0.17 | −27 |

*p < 0.05 relative to the control in the Mann-Whitney test.

A subject of the invention is also a pharmaceutical composition comprising an effective amount of at least one active principle chosen from a compound of formula I as described above, a compound of formula XVI:

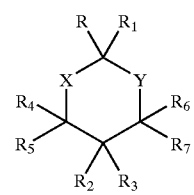

XVI in which R and $R_1$ together form one of the radicals:

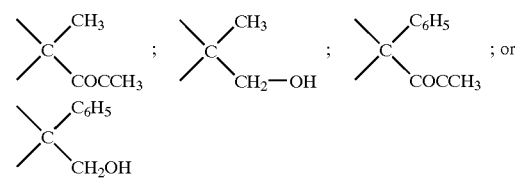

$R_2$, $R_3$, $R_5$ and $R_7$ represent a hydrogen atom;
X and Y represent an oxygen atom;
$R_4$ represents a methyl; and
$R_6$ represents a hydrogen atom or a methyl group;
and a pharmaceutically acceptable salt of these compounds, in combination with at least one pharmaceutically acceptable vehicle.

These compositions can be administered orally in the form of immediate-release or controlled-release granules, gelatin capsules or tablets, intravenously in the form of an injectable solution, transdermally in the form of an adhesive transdermal device, or locally in the form of a solution, cream or gel.

A solid composition for oral administration is prepared by adding a filler and, where appropriate, a binder, a crumbling agent, a lubricant, a dye or a flavour enhancer to the active principle and by shaping the mixture into a tablet, a coated tablet, a granule, a powder or a capsule.

Examples of fillers include lactose, corn starch, sucrose, glucose, sorbitol, crystalline cellulose and silicon dioxide, and examples of binders include poly(vinyl alcohol), poly(vinyl ether), ethylcellulose, methylcellulose, acacia, gum tragacanth, gelatin, shellac, hydroxypropylcellulose, hydroxypropylmethylcellulose, calcium citrate, dextrin and pectin. Examples of lubricants include magnesium stearate, talc, polyethylene glycol, silica and hardened plant oils. The dye can be any of those authorized for use in medicinal products. Examples of flavour enhancers include cocoa powder, mint in herbal form, aromatic powder, mint in oil form, borneol and cinnamon powder. Needless to say, the tablet or granule can be suitably coated with sugar, gelatin or the like.

An injectable form containing the compound of the present invention as active principle is prepared, where appropriate, by mixing the said compound with a pH regulator, a buffer, a suspending agent, a solubilizing agent, a stabilizer, a tonicity agent and/or a preserving agent, and by converting the mixture into a form for intravenous, subcutaneous or intramuscular injection, according to a standard process. Where appropriate, the injectable form obtained can be freeze-dried by a standard process.

Examples of suspending agents include methylcellulose, polysorbate-80, hydroxyethylcellulose, acacia, powdered gum tragacanth, sodium carboxymethylcellulose and polyethoxylated sorbitan monolaurate.

Examples of solubilizing agents include castor oil solidified with polyoxyethylene, polysorbate-80, nicotinamide, polyethoxylated sorbitan monolaurate and the ethyl ester of castor oil fatty acid.

In addition, the stabilizer includes sodium sulphite, sodium metasulphite and ether, while the preserving agent includes methyl p-hydroxybenzoate, ethyl p-hydroxybenzoate, sorbic acid, phenyl [sic], cresol and chlorocresol.

The invention is also directed towards the use of an active principle chosen from a compound of formula I as defined above, a compound of formula XVI as defined above, a compound of formula XVII:

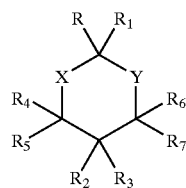

XVII in which

X and Y represent an oxygen atom;

$R_4$, $R_5$, $R_6$ and $R_7$ represent a hydrogen atom;

R represents pyridyl, piperidyl; pyridyl optionally substituted with one or more radicals chosen from a radical Z as defined above for formula I and a ($C_1$–$C_7$)alkylene chain; and piperidyl optionally substituted with one or more radicals chosen from a radical Z as defined above and a ($C_1$–$C_7$)alkylene chain; and $R_1$ represents phenyl optionally substituted with one or more radicals W as defined above for formula I; and a pharmaceutically acceptable salt of these compounds, for the preparation of a medicinal product intended to prevent or treat dyslipidaemia, atherosclerosis and diabetes.

The examples which follow illustrate the invention in a non-limiting manner.

The following abbreviations are used in the proton nuclear magnetic resonance (NMR) data: s for singlet, d for doublet, t for triplet, q for quartet, o for octet and m for multiplet. The chemical shifts δ are expressed in ppm; m.p. represents the melting point and b.p. represents the boiling point.

EXAMPLE 1

Methyl 2-Methyl-5,5-diphenyl[1,3]dioxane-2-carboxylate

A mixture of 22.8 g (0.1 M) of 2,2-diphenyl-1,3-propanediol and 100 g (0.98 M) of methyl pyruvate is brought to 70° C. in a 500 ml round-bottomed flask under a nitrogen atmosphere. 22.4 g (0.156 M) of $P_2O_5$ are added portionwise. An exothermic reaction takes place and the temperature rises to 98° C. The mixture is allowed to return to room temperature and is poured slowly into ice-cold water. This mixture is extracted with methylene chloride and the extracts are washed with sodium hydroxide and water. The extracts are concentrated and the residue is chromatographed by flash chromatography (70 $CH_2Cl_2$/50 cyclohexane eluent). The product is then recrystallized from 40 ml of diisopropyl ether. 7 g of a product of m.p. 116° C. are obtained.

EXAMPLE 2

2-Methyl-5,5-diphenyl[1,3]dioxane-2-carboxylic Acid 7 g of methyl 2-methyl-5,5-diphenyl[1,3]-dioxane-2-carboxylate are refluxed in the presence of 2.6 g of NaOH in a mixture of 120 ml of methanol and 30 ml of water. At the end of the reaction, the medium is concentrated and the solid obtained is dissolved in 300 ml of water. After acidification with HCl, the white solid formed is filtered off. It is recrystallized from a mixture of 50 ml of cyclohexane and 50 ml of diisopropyl ether. 4.1 g of a product of m.p. 148–150° C. are obtained.

EXAMPLE 3

Ethyl 2-(4-Chlorophenyl)-5,5-diphenyl[1,3]-dioxane-2-carboxylate 42.5 g (0.2 M) of ethyl 2-oxo-2-(4-chlorophenyl)acetate are placed in 400 ml of $CH_2Cl_2$ in a 500 ml reactor. 22.8 g (0.1 M) of 2,2-diphenylpropane-1,3-diol and then 14.2 g (0.1 M) of $BF_3.Et_2O$ are added. The mixture is left to react with stirring for 72 h at room temperature. The reaction mixture is taken up in $NaHCO_3$ solution. The organic phase is washed with saturated NaCl solution. After drying over $Na_2SO_4$ and concentration, a very thick oil is obtained. 150 ml of isopropyl ether are added and a white precipitate forms. After filtration, 30 g of product melting at 156–158° C. are obtained (yield: 71%).

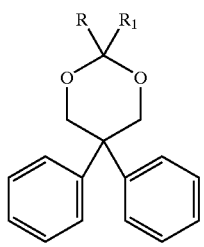

| Examples | R | R1 | m.p. °C. | NMR |
|---|---|---|---|---|
| 1 | CH$_3$ | COOCH$_3$ | 116 | CDCl$_3$: 1.37(3H, s); 3.72(3H,s); 4.14 (2H, d, J=11.8Hz); 4.49(2H, d, J=11.8 Hz); 6.88 to 7.35 (10H,m) |
| 2 | CH$_3$ | COOH | 148–150 | CDCl$_3$: 1.78(3H, s); 4.55(2H, d, J= 11.8Hz); 4.87(2H, d, J=11.8Hz); 7.25 to 7.67(10H, m) |
| 3 | 4-Cl-C$_6$H$_4$- | COOC$_2$H$_5$ | 156–158 | CDCl$_3$: 1.09(3H, t, J =7.1Hz); 4.1(2H, q, J=7.1Hz); 4.35(2H, d, J=11.8Hz); 4.53 (2H, d, J=11.8Hz); from 7 to 7.2(12H, m); from 7.38 to 7.41 (2H, m). |
| 4 | 4-OCH$_3$-C$_6$H$_4$- | COOH | 244–246 | DMSO d$_6$: 3.33(1H exchangeable with CF$_3$COOD); 4.35(2H, d, J=11.9Hz); 4.13 (2H, d, J=11.9Hz); 7.1 to 7.5(14H, m). |
| 5 | 4-OCH$_3$-C$_6$H$_4$- | COOC$_2$H$_5$ | 163 | CDCl$_3$: 1.08(3H, t, J= 7.1Hz); 3.64 (3H, s); 4.08(2H, q, J=7.1Hz); 4.35 (2H, d, J=11.8Hz); 4.5(2H, d, J= 11.8Hz); from 6.7 to 6.75(2H, m) from 7 to 7.2(10H, m); from 7.35 to 7.38(2H, m) |
| 6 | 4-OCH$_3$-C$_6$H$_4$- | COOH | 225 | DMSO d$_6$: 3.73(3H, s); 4.33(2H, d, J=11.92Hz); 4.88 (2H, d, J=11.9Hz); from 6.88 to 6.91(2H, m); from 7.13 to 7.45 (12H, m) |
| 7 | 4-CH$_3$-C$_6$H$_4$- | COOC$_2$H$_5$ | 151 | CDCl$_3$: 1.36(3H; t, J= 7.1Hz); 2.47 (3H, s); 4.37(2H, q, J =7.1Hz); 4.64(2H, d, J=11.8Hz); 4.8 (2H, d, J=11.8Hz); from 7.28 to 7.48 (12H, m); from 7.6 to 7.63(2H, m) |

-continued

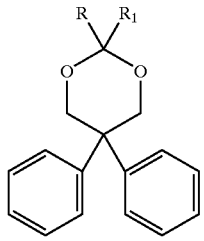

| Examples | R | R1 | m.p. °C. | NMR |
|---|---|---|---|---|
| 8 | 4-methylphenyl | COOH | 193 | DMSO $d_6$: 2.02(3H, s); 4.10(2H, d, J=11.8 Hz); 4.64(2H, d, J=11.8Hz); from 6.89 to 7.2(14H, m) |
| 9 | 2-thienyl | COOC$_2$H$_5$ | 190–191 | CDCl$_3$: 1.3(3H, t, J=7.1Hz); 4.32(2H, q, =7.1Hz); 4.5(2H, d, J=11.8Hz); 4.71(2H, d, J=11.8Hz); from 6.96 to 7(1H, m); from 7.2 to 7.4 (12H, m) |
| 10 | 2-thienyl | COOH | 193 | DMSO $d_6$: 4.16(2H, d, J=12Hz); 4.72(2H, d, J 32 12.0Hz); from 6.82 to 7.36(13H, m) |
| 11 | H | COOC$_2$H$_5$ | 60 | CDCl$_3$: 1.27(3H, t, J=7.1Hz); 4.18 to. 4.37(4H, m); 4.87 (2H, d, J=11.6Hz); 5.21(1H, s); 7.18 to 7.55(10H, m) |
| 12 | H | COOH | 158–160 | CDCl$_3$: 4.25(2H, d, J=11.6Hz); 4.78(2H, d, J=11.6Hz); 5.13 (1H, s); 7.04 to 7.42 (10H, m) |
| 13 | phenyl | COOC$_2$H$_5$ | 182 | CDCl$_3$: 1.17(3H, t, J=7.1Hz); 4.26(2H, q, J=7.1Hz); 4.55 (2H, d, J=11.8Hz); 4.71(2H, d, J=11.8 Hz); 7.29 to 7.70 (15H, m) |
| 14 | phenyl | COOH | 211–213 | CDCl$_3$: 4.56 to 4.65 (4H, m); 7.22 to 7.62 (15H, m) |
| 15 | 4-fluorophenyl | COOC$_2$H$_5$ | 152 | CDCl$_3$: 1.08(3H, t, J=12Hz); 4.09(2H, q, J=7.1Hz); from 4.32 to 4.36(2H, m); 4.53 (2H, d, J=11.9Hz); from 6.84 to 6.9(2H, m); from 7.08 to 7.2 (10H, m); from 7.4 to 7.43(2H, m) |

-continued

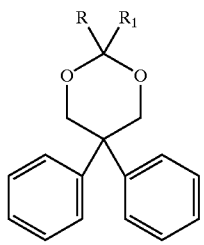

| Examples | R | R1 | m.p. ° C. | NMR |
|---|---|---|---|---|
| 16 | 4-F-C6H4- | COOH | 234–235 | DMSO $d_6$: 4.42(2H, d, J=11.9Hz); 5.01 (2H, d, J=11.9Hz); from 7.21 to 7.61 (14H, m) |
| 17 | 5,5,8,8-tetramethyl-5,6,7,8-tetrahydronaphthalen-2-yl | COOC$_2$H$_5$ | 115–116 | CDCl$_3$: 1.15 to 1.20 (15H, m); 1.57(4H, s); 4.19(2H, q, J=7.1Hz); 4.42(2H, d, J=11.7Hz); 4.58 (2H, d, J=11.7Hz); 7.1 to 7.3(12H, m); 7.4(1H, s) |
| 18 | furan-2-yl | COOC$_2$H$_5$ | 163 | CDCl$_3$: 1(3H, t, J=7.1Hz); 4.12(2H, q, J=7.1Hz); 4.3(2H, d, J=11.7Hz); 4.43 (2H, d, J=11.7Hz); 6.2(1H, m); 6.4(1H, d); from 7 to 7.14 (10H, m); 7.25(1H, d, J=0.7Hz) |
| 19 | 3-Cl-C6H4- | COOC$_2$H$_5$ | 145–150 | CDCl$_3$: 1.43(3H, t, J=7.1Hz); 4.44(2H, q, J=7.1Hz); 4.7 (2H, d, J=11.8Hz) 4.9(2H, d, J =11.8 Hz); from 7.4 to 7.55 (12H, m); 7.65 to 7.7 (1H, m); from 7.8 to 7.83(1H, m) |
| 20 | 3-Cl-C6H4- | COOH | 252 | DMSO $d_6$: 3.3(1H, s); 4.3(2H, d, J=11.9 Hz); 4.9(2H, d, J=11.9Hz); from 7.1 to 7.46 (14H, m) |
| 21 | isopropyl | COOC$_2$H$_5$ | 103 | CDCl$_3$: 0.98(6H, d, J=6.9Hz); 1.52(3H, t, J=7.1Hz); 2.17 (1H, sept, J=6.9 Hz); from 4.43 to 4.5 (4H, m); 4.85(2H, d, J =11.9Hz); from 7 17 to 7.2(2H, m); from 7.37 to 7.52(6H, m); from 7.62 to 7.65 (2H, m) |

-continued

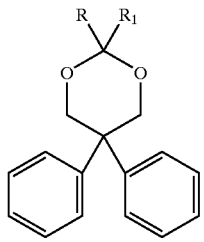

| Examples | R | R1 | m.p. °C. | NMR |
|---|---|---|---|---|
| 22 | benzyl (PhCH$_2$) | COOC$_2$H$_5$ | 102 | CDCl$_3$: 1.25(3H, t, J=7.1Hz); 1.93 to 1.99(2H, m); 2.48 to 2.54(2H, m); 4.17 to 4.27(4H, m); 4.62 (2H, d, J=11.5Hz); 6.93 to 7.43(15H, m) |
| 23 | benzyl (PhCH$_2$) | COOH | 197–198 | CDCl$_3$: 2.03 to 2.09 (2H, m); 2.46 to 2.60 (2H, m); 4.33(2H, d, J =11.8Hz); 4.69 (2H, d, J =11.8Hz); 6.87 to 7.57(15H, m) |
| 24 | 4-biphenylyl | COOC$_2$H$_5$ | 209 | CDCl$_3$: 1.31(3H, t, J=7.1Hz); 4.32(2H, q, J=7.1Hz); 4.6 (2H, d, J=11.7Hz); 4.8(2H, d, J=11.7 Hz); from 7.05 to 7.75 (19H, m) |
| 25 | 3,4-dichlorophenyl | COOC$_2$H$_5$ | 108 | CDCl$_3$: 1.45(3H, t, J=7.1Hz); 4.45(2H, q, J=7.1Hz); 4.69 (2H, d, J=11.8Hz); 4.89(2H, d, J=11.8 Hz); 7.20 to 7.65 (12H, m); 7.92(1H, d, J=1.7Hz) |
| 26 | 3,4-dichlorophenyl | COOH | 217–219 | DMSO d$_6$: 4.26(2H, d, J=11.8Hz); 4.83 (2H, d, J=11.8Hz); from 7.1 to 7.54(19H, m) ; 13.4 (1H, s, exchangeable with CF$_3$COOD) |
| 27 | 4-biphenylyl | COOH | 261 | DMSO d$_6$: 4.26(2H, d, J=11.8Hz); 4.83 (2H, d, J=11.8HZ); from 7.1 to 7.54(19H, m); 13.4(1H, s, exchangeable with CF$_3$COOD) |

-continued

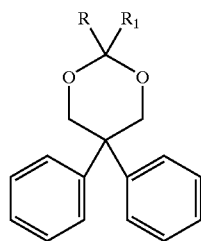

| Examples | R | R1 | m.p. ° C. | NMR |
|---|---|---|---|---|
| 28 | 4-Cl-phenyl | CH$_2$—COOC$_2$H$_5$ | Boiling point: b.p.$_{0.5}$ = 120.90 | CDCl$_3$: 0.82(3H, t, J=7.1Hz); 2.54(2H, s); 3.64(2H, q, J=7.1Hz); 3.95 to 4.02 (2H, m); 4.4(2H, d, J=11.6Hz); from 6.7 to 6.75(2H, m); from 6.96 to 7.34(12H, m) |
| 29 | 4-Cl-phenyl | CH$_2$COCH | 227 | DMSO d$_6$: 2.76(2H, s); 4.11(2H, d, J=11.5 Hz); 4.85 (2H, d, J=11.57Hz); from 6.96 to 7.16(14H, m); 12.1 (1H, s, exchangeable with CF$_3$COOD) |
| 30 | cyclohexyl | COOC$_2$H$_5$ | 170 | CDCl$_3$: 1.1 to 1.3(5H, m); 1.47(3H, t, J=7.1Hz); from 1.67 to 1.9(6H, m); from 4.3 to 4.5(4H, m); 4.78 (2H, d, J=11.8Hz); from 7.1 to 7.15(2H, m); from 7.29 to 7.47 (6H, m); from 7.56 to 7.59(2H, m) |
| 31 | 2-COOEt-phenyl | H | 102 | CDCl$_3$: 1.25(3H, t, J=7.1Hz); 4.2(2H, q, J=7.1Hz); 4.33(2H, d, J=11.4Hz); 4.71 (2H, d, J=11.4Hz); 6.35(1H, s); 6.96 to 7.70(14H, m) |
| 32 | 2-COOH-phenyl | H | 174–176 | CDCl$_3$: 4 46(2H, d, J=11.4Hz), 4.85(2H, d, J=11.4 Hz); 6.51 (1H, s); 7.07 to 7.53 (12H, m); 7.74(1H, d, J=7.8Hz); 7.97(1H, d, J=7.8Hz) |
| 33 | 5,5,8,8-tetramethyl-5,6,7,8-tetrahydronaphthyl | COOH | 216–217 | DMSO d$_6$: 1.34(6H, s); 1.37(6H, s): 1.8 (4H); 4.5(2H, d, J=11.8Hz); 5.1(2H, d, J=11.8Hz); from 7.33 to 7.7(13H, m) |
| 34 | furan-2-yl | COOH | 187 | CDCl$_3$: 4.75(2H, d, J=11.6Hz); 4.82(2H, d, J=11.6Hz); 6.6 (1H, m); 6.8(1H, m); from 7.3 to 7.5 (10H, m); 7.66(1H, m); 8.5 (1H exchangeable with CF$_3$COOD) |

-continued

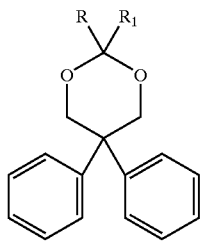

| Examples | R | R1 | m.p. ° C. | NMR |
|---|---|---|---|---|
| 35 | 1-naphthyl | COOC₂H₅ | 172 | CDCL₃: 1.01(3H, t, J=7.1Hz); 4.07(2H, q, J=7.1Hz); 4.57 (2H, d, J=11.6Hz); 4.65(2H, d, J=11.6 Hz); 7.03 to 7.46 (13H, m); 7.76(2H, m); 7.87(1H, d, J=7.4Hz); 8.59(1H, m) |
| 36 | 1-naphthyl | COOH | 248 | DMSO d₆: 4.8(2H, d, J=11.8Hz); 5.11(2H, d, J=11.8Hz); 7.2 to 7.7(13H, m); 8.01 (3H, m); 8.75(1H, d, J=8.3Hz); 13.6(1H, exchangeable with CF₃COOD) |
| 37 | isopropyl (H₃C)₂CH– | COOH | 137 | CDCl₃: 1(6H, J=6.9 Hz); 2.2(1H, m); 4.5 (2H, d, J=11.9Hz); 4.9(2H, d, J=11.9 Hz) from 7.2 to 7.22 (2H, m); from 7.4 to 7.5(6H, m); from 7.6 to 7.65 (2H, m) |
| 38 | 4-chlorophenyl | CH₂OH | 120–122 | DMSO d₆: from 3.3 to 3.4(2H, m); 4(2H, d, J=11.4Hz); 4.8(2H, d, J=11.4Hz); from 4.9 to 4.92(1H, m, exchangeable with D₂O); from 7 to 7.6 (1H, m) |
| 39 | cyclohexyl | COOH | 240 | DMSO d₆: from 1.03 to 1.24(5H, m); from 1.6 to 1.7(6H, m); 4.21 (2H, d, J=11.6Hz); 4.9(2H, d, J=11.8 Hz); from 7.2 to 7.7 (10H, m) |
| 40 | 4-chlorophenyl | =CH–N-piperidinyl | 230–232 | DMSO d₆: 1.0(2H, m); 1.4(4H, m); 3.3(2H, m); 3.5(2H, m); 4.4 (2H, d, J=11.4Hz); 4.9(2H, d, J=11.4. Hz); 7.32–7.2(10H, m); 7.4–7.5(4H, m) |
| 41 | phthalimido-CH₂– | CH₃ | 145 | CDCl₃: 1.6(3H, s); 4.0(2H, s); 4.5(2H, d, J=11.8Hz); 4.7 (2H, d, J=11.8Hz); 6.3–6.8(10H, m); 7.0–7.8(4H, m) |

-continued

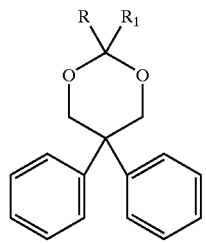

| Examples | R | R1 | m.p. ° C. | NMR |
|---|---|---|---|---|
| 42 | (ethyl ester of methyl-pentadienoate with p-phenyl linker) | H | 115–117 | CDCl₃: 1.2(3H, m); 2.0(3H(Z), s); 2.3 (3H(E), s); 4.1(2H, m); 4.3(2H, d, J=10.7Hz), 4.8(2H, d, J=10.7Hz); 5.6(1H, s); 5.7(1H(Z), s); 5.8(1H(E), s); 6.7–6.8(2H, m); 7.0–7.5 (14H, m) |
| 43 | (carboxylic acid of methyl-pentadienoate with p-phenyl linker) | H | 220–222 | DMSO d₆: 1.4(3H, s, Z form); 2.3(3H, s, E form); 4.4(2H, d, J=11Hz); 5.0(2H, d, J=11Hz); 5.7(1H, s); 6.0((1H, s); 7.0–7.6 (16H, m); 8.3(1H, d, Z form, J=16Hz) |
| 44 | 4-Cl-phenyl | CONH—CH₂—COOC₂H₅ | 195–197 | CDCl₃: 1.15(3H, t, J=7.1Hz); 3.9(2H, d, J=5.4Hz); 4.1(2H, q, J=7.1Hz); 4.4(2H, d, J=11.6Hz); 4.5(2H, d, J=11.6 Hz); 6.9(1H, m); 7.3–7.1(12H, m); 7.5(2H, d, J=8.7Hz) |
| 45 | 4-Cl-phenyl | CO(NH)—CH₂COOH | 258–260 | DMSO d₆: 4.0(2H, d, J=6.02Hz); 4.8(2H, d, J=11.7Hz); 5.0 (2H, d, J=11.7Hz); 7.4–7.7(14H, m); 8.9 (1H exchangeable, t, J=6.0Hz) |
| 46 | 4-CF₃-phenyl | COOC₂H₅ | 145 | CDCl₃: 1.1(3H, t, J=7.1Hz); 4.11(2H, q, J=7.1Hz); 4.38(2H, d, J=11.9Hz); 4.57 (2H, d, J=11.9Hz); 7 to 7 23(10H, m) 7.47(2H, d, J=8.4 Hz); 7.6(2H, d, J = 8.4Hz) |

-continued

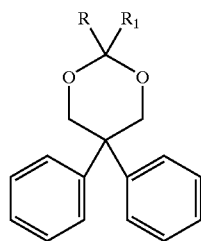

| Examples | R | R1 | m.p. ° C. | NMR |
|---|---|---|---|---|
| 47 | H | O=C(OH)(OCH)(H₃C) attached to 4-phenoxy | 168–170 | CDCl₃: 1.58(6H, s); 4.42(2H, d, J=11.5 Hz); 4.88(2H, d, J=11.5Hz); 5.63(1H 6.91 to 7.57(14H, m) |
| 48 | CF₃-phenyl-CH₂ (4-trifluoromethylbenzyl) | COOH | 210 | DMSO d₆: 4.37(2H, d, J=11.9Hz); 4.96 (2H, d, J=11.9Hz); 7.09 to 7.45(10H, m); 7.65 to 7.5(4H, m); 13.7(1H, s, exchangeable with TFA) |

EXAMPLE 42

Ethyl 5-[4-(5,5-Diphenyl[1,3]dioxan-2-yl)-phenyl]-3-methylpenta-2,4-dienoate

The following are placed in a 250 ml reactor fitted with Dean-Stark apparatus: 70 ml of toluene, 3.5 g (0.011 M) of ethyl 5-(4-diethoxymethylphenyl)-3-methylpenta-2,4-dienoate, 5.0 g (0.011 M) of 2,2-diphenylpropanediol and finally 0.5 g of para-toluenesulphonic acid.

The mixture is refluxed for 1 h while removing the first fractions distilled. After cooling to room temperature, the reaction medium is washed with 5% NaHCO₃ solution. The organic phase is separated out after settling has taken place and dried over Na₂SO₄. After concentration to dryness, a thick oil is obtained.

The product is purified by flash chromatography with a mixture of 95 cyclohexane/5 ethyl acetate as eluent.

3.5 g of product are thus obtained in the form of a foam which is recrystallized from diisopropyl ether to give 2.3 g of product melting at 115–117° C.

EXAMPLE 52

Ethyl 3,3'-bis(4-Fluorophenyl)oxirane-2-carboxylate 23.6 ml (0.220 M) of ethyl chloroacetate and 30 g (0.137 M) of 4,4'-difluorobenzophenone are introduced into 80 ml of tetrahydrofuran in a 500 ml round-bottomed flask under a nitrogen atmosphere. A total of 8.8 g of 60% sodium hydride is added portionwise to this medium every 30 minutes. At the end of the addition, an exothermic reaction takes place during which the reaction is maintained at 40–45° C. by an ice bath. After leaving overnight at room temperature, the medium is hydrolyzed by addition of dilute hydrochloric acid and then extracted with ether. After concentration, 62 g of an orange-coloured oil are obtained, which product is purified by flash chromatography (70 cyclohexane/30 CH₂Cl₂ eluent). 34.7 g of a product which crystallizes slowly are thus obtained, and this product is finally triturated from 40 ml of pentane. A further flash chromatography (95 cyclohexane/5 diisopropyl ether eluent) gives 27.5 g of pure ester.

NMR (CDCl₃): 0.88 (3H, t, J=7.1 Hz); 3.81 (1H, s); 3.83 to 3.93 (2H, m); 6.85 to 6.95 (4H, m); 7.11 to 7.16 (2H, m); 7.25 to 7.30 (2H, m).

2-bis(4-Fluorophenyl)ethanal 27.5 g of ethyl 3,3'-bis(4-fluorophenyl)-oxirane-2-carboxylate in 210 ml of ethanol are refluxed for 8 hours in the presence of 55 ml of KOH (at 20% in water) in a 500 ml round-bottomed flask. The reaction medium is concentrated and the residue is taken up in 600 ml of water. An insoluble material is removed by filtration and the filtrate is acidified with hydrochloric acid and extracted with ether. The oil obtained after concentration is treated (oil bath) at 150° C. for one hour. 17.5 g of 2-bis(4-fluorophenyl)ethanal are thus obtained.

NMR (CDCl₃): 4.88 to 4.89 (1H, m); 7.04 to 7.20 (8H, m); 9.89 to 9.90 (1H, m)

2,2'-bis(4-Fluorophenyl)-1,3-propanediol

A mixture of 17.5 g of 2-bis(4-fluorophenyl)-ethanol, 16.1 ml (0.153 M) of 37% formaldehyde, 7.6 g of potassium carbonate, 18 ml of water and 70 ml of ethanol is refluxed for 7 hours in a 250 ml round-bottomed flask. After concentration of the medium, the residue is taken up in 200 ml of water and extracted with methylene chloride, which is concentrated. 21.1 g of an oil are obtained and this product is purified by flash chromatography (eluent: 98 methylene chloride/2 methanol). 17.8 g of 2,2'-(4-fluorophenyl)-1,3-propanediol [sic] are thus obtained (m.p.=74° C.).

NMR (CDCl$_3$): 2.16 to 2.18 (2H, m, exchangeable with D$_2$O); 4.11 to 4.21 (4H, m); 6.91 to 7.18 (8H, m).

Ethyl 2-(4-Chlorophenyl)-5,5-bis(4-fluoro-phenyl)-(1,3] dioxane-2-carboxylate (Example 51)

1.7 g of para-toluenesulphonic acid in 120 ml of toluene are refluxed for 30 minutes in a 250 ml round-bottomed flask fitted with Dean-Stark apparatus. 8 g (0.0302 M) of 2,2'-bis (4-fluorophenyl)-1,3-propanediol and 7 g (0.0332 M) of ethyl (4-chlorophenyl)-oxoacetate are added and the mixture is refluxed for 8 hours. The reaction medium is cooled, diluted with 200 ml of ethyl ether, washed with normal sodium hydroxide and the organic phase is separated out after settling has taken place, dried and concentrated. The residue is washed with isooctane and then recrystallized from isopropyl ether. A white solid of m.p. 150° C. is thus obtained.

2-(4-Chlorophenyl)-5,5-bis(4-fluorophenyl)-[1,3] dioxane-2-carboxylic Acid (Example 52)

2.8 g of ethyl 2-(4-chlorophenyl)-5,5-bis(4-fluorophenyl)-[1,3]dioxane-2-carboxylate are refluxed for 7 hours in 60 ml of methanol and 15 ml of water containing 0.7 g of NaOH. After concentrating, the residue is diluted with water and stirred until a solution is obtained. This solution is washed with ether and the aqueous phase is acidified with HCl. The solid formed is filtered off and washed with water and pentane. The product is recrystallized from 100 ml of toluene. (m.p.=228–30° C.; weight obtained 1.9 g).

EXAMPLE 54

Ethyl 3,3'-bis(3-Trifluoromethylphenyl)oxirane-2-carboxylate 5.9 g of 60% sodium hydride are introduced in 3 portions, every 30 minutes, into a 500 ml round-bottomed flask under a nitrogen atmosphere and containing 16.2 ml (0.15 M) of ethyl chloroacetate, 29.9 g (0.0938 M) of 3,3'-bis (trifluoromethyl)benzophenone and 80 ml of tetrahydrofuran, at 40° C. The mixture is left stirring for a further 2 hours at 40° C. and then overnight at room temperature. The medium is hydrolysed with 50 ml of HCl and then extracted with ether. The extracts are washed with water, dried and concentrated. The oil obtained is purified by flash chromatography (eluent: 95 cyclohexane/5 isopropyl ether). 31 g of the ethyl ester are obtained.

NMR (CDCl$_3$): 0.89 to 0.93 (3H, m); 3.90 to 3.98 (3H, m); 7.38 to 7.66 (8H, m).

2-bis(3-Trifluoromethylphenyl)ethanal

A mixture of 31 g of ethyl 3,3'-bis(3-trifluoromethylphenyl)oxirane-2-carboxylate and 56.7 ml of aqueous 20% KOH solution in 210 ml of ethanol is refluxed for 8 hours. The reaction medium is concentrated and the residue is taken up in water and washed with ether. The aqueous phase is acidified and extracted with ether. The residue is heated on an oil bath at 150° C. for one hour. The crude product is purified by flash chromatography (eluent: 70 CH$_2$Cl$_2$/30 heptane) to give 15.5 g of 2-bis(3-trifluoromethyl-phenyl)ethanal.

NMR (CDCl$_3$): 4.86 to 4.89 (1H, m); 7.06 to 7.88 (8H, m); 9.77 to 9.78 (1H, m).

2-bis(3-Trifluoromethylphenyl)-1,3-propanediol

A mixture of 12.2 g of 2-bis(3-trifluoromethylphenyl) ethanal, 7.7 ml of 37% formaldehyde, 3.5 g of potassium carbonate, 8.8 ml of water and 35 ml of ethanol is refluxed in a 500 ml round-bottomed flask for 6 hours. The reaction medium is concentrated and the residue is diluted with water and extracted with ether. After concentrating, the residue is purified by flash chromatography (eluent: 98 CH$_2$Cl$_2$/2 MeOH). After trituration from 20 ml of pentane, 5 g of 2-bis(3-trifluoromethylphenyl)-1,3-propanediol are obtained (m.p.=70° C.).

NMR (CDCl$_3$): 2.35 (2H, m, exchangeable with D$_2$O); 4.26 (4H, m); 7.18 to 7.48 (8H, m).

Ethyl 2-(4-Chlorophenyl)-5,5'-bis(3-trifluoro-methylphenyl)-[1,3]dioxane-2-carboxylate (Example 53)

1.2 g of para-toluenesulphonic acid in 90 ml of toluene are refluxed in a 250 ml round-bottomed flask fitted with Dean-Stark apparatus. 4.9 g of ethyl (4-chlorophenyl) oxoacetate and 7.1 g of 2-bis(3-trifluoromethylphenyl)-1,3-propanediol are added. Refluxing is continued for 8 hours. The reaction medium is cooled, diluted with 150 ml of diethyl ether, washed with 1N sodium hydroxide and dried. The residue obtained is purified by flash chromatography (eluent: 95 CH$_2$Cl$_2$/5 heptane). 2.8 g of product are obtained (m.p.=110° C.).

2-(4-Chlorophenyl)-5,5'-bis(3-trifluoromethyl-phenyl)-[1,3]dioxane-2-carboxylic Acid (Example 54)

2.8 g of the above ester are treated at reflux for 5 hours in 60 ml of methanol, 15 ml of water and 0.6 g of NaOH. The reaction medium is concentrated and the residue is taken up in 100 ml of water. After washing with ether, the aqueous phase is acidified with hydrochloric acid. It is extracted with ether, the extracts are concentrated and the product is recrystallized from toluene. 1.4 g of product of m.p.= 197–199° C. are obtained.

EXAMPLE 55

Diethyl 2-(9H-Fluoren-9-yl)malonate 16.3 g (0.051 M) of ethyl malonate in 300 ml of toluene are introduced into a 500 ml reactor under a nitrogen atmosphere. 4.6 g (0.056 M) of 60% NaH in oil are added portionwise at room temperature. The temperature rises to 32° C. The reaction medium is then maintained at 80° C. for 15 minutes. A white broth forms.

A solution of 25 g (0.051 M) of 9-bromofluorene in 60 ml of toluene is added at this temperature. The mixture is left to react for 8 h at 80° C. 100 ml of ice-cold water are added at a temperature below 20° C. The organic phase is separated out after settling has taken place and washed with water. It is dried over Na$_2$SO$_4$ and concentrated to dryness. An oil (31 g) which crystallizes is obtained.

Recrystallization is carried out in 160 ml of diisopropyl ether to give 23.7 g of a product melting at 71° C. (70% yield).

NMR (CDCl$_3$): 1.0 (3H, t, J=7.1 Hz); 3.9 (1H, d, J=5.5 Hz); 4.0 (2H, q, J=7.1 Hz); 4.6 (1H, d, J=5.5 Hz); 7.1–7.3 (4H, m); 7.5 (2H, d, J=7.4 Hz); 7.7 (2H, d, J=7.4 Hz).

2-(9H-Fluoren-9-yl)propane-1,3-diol 200 ml of anaesthetic ether and then 4.5 g (0.118 M) of LiAlH$_4$ are placed in a 500 ml reactor under a nitrogen atmosphere. A solution of 9.6 g (0.0296 M) of diethyl 2-(9H-fluoren-9-yl)malonate in 100 ml of anaesthetic ether is added at a temperature below 20° C. The mixture is left to react for 2 h at room temperature and then refluxed for 2 h.

The reaction medium is cooled to 0° [lacuna] and 100 ml of water are added cautiously. This mixture is acidified with dilute $H_2SO_4$ and extracted with ethyl acetate. The extracts are washed with water and then concentrated to dryness, after drying over sodium sulphate. An oil is obtained which is recrystallized from 130 ml of isopropyl ether. 6.3 g of a white solid melting at 101° C. are obtained (88% yield).

NMR ($CDCl_3$): 2.2 (2H, s, exchangeable with $D_2O$); 2.9 (1H, m); 3.8–4.0 (4H, m); 4.3 (1H, d, J=2.7 Hz); 7.4–7.6 (4H, m); 7.7 (2H, d, J=7.4Hz); 7.9 (2H, d, J=7.4 Hz).

Ethyl 2-(4-Chlorophenyl)-5-(9H-fluoren-9-yl)-[1,3] dioxane-2-carboxylate (Example 55)

The product is obtained by reacting the above diol with ethyl 2-(4-chlorophenyl)-2-oxoacetate according to the method already described, by refluxing in toluene in the presence of para-toluenesulphonic acid.

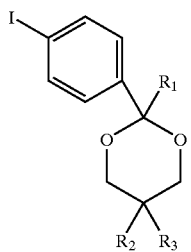

| Examples | R2 | R3 | R1 | m.p. ° C. | NMR |
|---|---|---|---|---|---|
| 49 | 4-Cl-C$_6$H$_4$ | 4-Cl-C$_6$H$_4$ | COOC$_2$H$_5$ | 170 | CDCl$_3$: 1.14(3H, t, J=7.1Hz); 4.1(2H, q, J=7.1Hz); 4.32 to 4.50(4H, m); 6.98 to 7.46 (12H, m) |
| 50 | 4-Cl-C$_6$H$_4$ | 4-Cl-C$_6$H$_4$ | COOH | 259–261 | DMSO d$_6$: 4.54 (2H, d, J=11.9Hz); 5.12(2H, d, J=11.9Hz); 7.45 to 7.71(12H, m); 13.8(1H, s, exchangeable with CF$_3$COOD) |
| 51 | 4-F-C$_6$H$_4$ | 4-F-C$_6$H$_4$ | COOC$_2$H$_5$ | 150 | CDCl$_3$: 1.27(3H, t, J=7.1hz); 4.35(2H, q, J=7.1Hz); 4.55(2H, d, J=11.8Hz); 4.70 (2H, d, J=11.8 Hz); 7.11 to 7.75 (12H, m) |
| 52 | 4-F-C$_6$H$_4$ | 4-F-C$_6$H$_4$ | COOH | 228–230 | CDCl$_3$: 4.39 to 4.42(4H, m); 6.84 to 7.49 (12H, m) |
| 53 | 3-CF$_3$-C$_6$H$_4$ | 3-CF$_3$-C$_6$H$_4$ | COOC$_2$H$_5$ | 110 | CDCl$_3$: 1.16 (3H, t, J= 7.1Hz); 4.17 (2H, q, J=7.1 Hz); 4.42(2H, d,nl J=11.8Hz) 4.56(2H, d, J= 11.8Hz); 7.18 to 7.54(12H, m) |

-continued

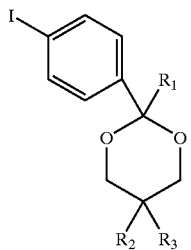

| Examples | R2 | R3 | R1 | m.p. °C. | NMR |
|---|---|---|---|---|---|
| 54 | 3-CF₃-C₆H₄-CH₂- | 3-CF₃-C₆H₄-CH₂- | COOH | 197–199 | CDCl₃: 4.69 (2H, d, J=11.6 Hz); 4.75(2H, d, J=11.6Hz); 7.47 to 7.79 (12H, m) |
| 55 | 9-fluorenyl- | H | COOC₂H₅ | 151 | CDCl₃: 1.07 (3H, t, J= 7.1Hz); from 2.84 to 2.95(1H, m); from 3.82 to 3.95(5H, m); 4.07(2H, q, J= 7.1Hz); from 7.2 to 7.5(10H, m); 7.7(2H, d, J= 7.3Hz) |
| 56 | —(CH₂)₄— (cyclopentane) | | COOC₂H₅ | 117 | CDCl₃: 1.14 (3H, t, J= 7.1Hz); from 1.64 to 1.7(2H, m); from 1.8 to 1.92(4H, m); 3.74(2H, d, J= 11.6Hz); 3.87 (2H, d, J=11.6 Hz); 4.13(2H, q, J=7.1Hz); from 7.2 to 7.28(2H, m); from 7.47 to 7.5(2H, m) |
| 57 | —(CH₂)₄— (cyclopentane) | | COOH | 171 | CDCl₃: 1.7 to 1.9 (6H, m); 3.84 (2H, d, J=3 Hz); 3.76(2H, d, J=11.3Hz); 7.28(2H, d, J= 7.6 Hz); 7.49 (2H, d, J=6.93 8.5(1H, s) |
| 58 | C₆H₅-CH₂- | C₆H₅-CH₂- | COOH | 198–200 | DMSO: 2.32 (2H, s); 2.72 (2H, s); 3.53 (4H, s); 6.88– 7.40(14H, m) |

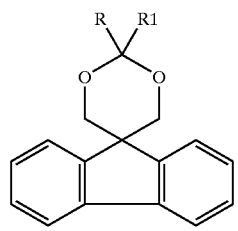

| Examples | R | R1 | m.p. (° C.) | NMR |
|---|---|---|---|---|
| 59 | —CH₃ | —COOCH₃ | 110 | CDCl₃: 1.8(3H, s); 3.65(2H, d, J=10 Hz); 3.95(3H, s) 4.45(2H, d, J=10 Hz); 7.2 to 8.4(m) |
| 60 | —CH₃ | —COOH | 199–202 | DMSO d₆: 1.7(3H, s); 3.5(2H, d, J=12 Hz); 4.4(2H, d, J=12Hz); 7.2 to 8.4 (8H, m) |
| 61 | —CH₃ | —CH₂—COOC₂H₅ | Eb/0.2 mm Hg = 180–190 | CCl₄: 1.3(3H, t); 1.9 (3H, s); 3.15(2H, s); 3.8 to 4.9(6H, m); 7.0 to 8.0(8H, m) |
| 62 | —CH₃ | —CH₂—COOH | 106–110 | CDCl₃: 1.9(3H, s); 3.2(2H, s); 4.1 (4H, s); 7.1 to 8 (8H, m); 10.0(1H, exchangeable with D₂O) |
| 63 | —CH₂—CH₂—COOCH₃ | COOCH₃ | 120 | CDCl₃: 2.3 to 2.95 (4H, m); 3.7(2H, d, J=10Hz); 3.8 (3H, s); 4.0(3H, s); 4.45(2H, d, J=10Hz); 7.2 to 8.4(8H, m) |
| 64 | —CH₂—CH₂—COOH | —COOH | 226–228 (hemi-hydrate) | CDCl₃: 2.2 to 3.0 (4H, m); 3.65(2H, d, J=11Hz); 4.6 (2H, d, J= Hz); 7.0 to 8.4 (8H, m); 10.9(2H, exchangeable with D₂O) |
| 65 | 4-COOCH₃-C₆H₄— | CH₃ | 132–134 | CDCl₃: 1.85(3H, s); 3.6(2H, d, J=12Hz); 4.05 (3H, s); 4.35(2H, d, J=12Hz); 6.8 to 8.5(12H, m) |
| 66 | H | —COO—nbutyl | Eb/0.2 mm Hg 170–195 m.p. = 80° C. | CCl₄: 0.8 to 2.1 (7H, m); 3.8 to 4.16(6H, m); 5.25 (1H, s); 7 to 8.5 (8H, m) |
| 67 | H | —COOH | 158–160 | CDCl₃: 4.0(2H, d, J=10Hz); 4.45 92H, d, J=10 Hz); 5.5(1H, s) 6.9 to 8.4(8H, m); 10.4(1H, exchangeable with D₂O) |

-continued

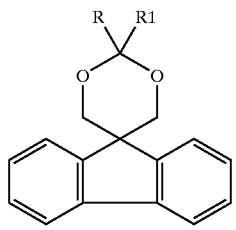

| Examples | R | R1 | m.p. (° C.) | NMR |
|---|---|---|---|---|
| 68 | phenyl | —COOCH₃ | 204 | CDCl₃: 3.85(3H, s); 3.95(2H, d, J=12Hz); 4.4(2H, d, J=12Hz); 6.8 to 8.2(13H, m) |
| 69 | phenyl | —COOH | 193–195 | CDCl₃: 4.05(2H, d, J=12Hz); 4.4 (2H, d, J=12 Hz); 7.0 to 8.2 (13H, m); 9.2(1H, exchangeable with D₂O) |
| 70 | 4-CH₃-phenyl | —COOC₂H₅ | 152–154 | CDCl₃: 1.1 to 1.6 (3H, m); 2.4(3H, s); 3.7 to 4.7 (6H, m); 7.1 to 8.1(12H, m) |
| 71 | 4-OCH₃-phenyl | —COOC₂H₅ | 200 | CDCl₃: 1.3(3H, t); 3.8 to 4.6(9H, 6.8 to 8.0 (12H, m) |
| 72 | 4-OCH₃-phenyl | —COOH | 208 | CDCl₃: 3.85(2H, d, J=12Hz); 3.85 (3H, s); 4.45(2H, d, J=12Hz); 6.6 to 8.O (13H, 1H exchangeable with D₂O) |
| 73 | 4-Cl-phenyl | —COOC₂H₅ | 178 | DMSO d₆: 1.1(3H, t, J=7Hz); 3.6 to 4.8(6H, m); 7.0 to. 8.2(12H, m) |
| 74 | 4-Cl-phenyl | —COOH | 240–242 | DMSO d₆: 3.75(2H, d, J=12Hz); 4.55(2H, d, J=12Hz); 7.0 to 8.4 (12H, m) |

-continued

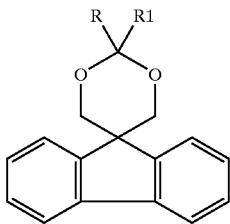

| Examples | R | R1 | m.p. (° C.) | NMR |
|---|---|---|---|---|
| 75 | (thiophene) | —COOC₂H₅ | 130 | CDCl₃: 1.45(3H, t, J=7Hz); 3.8 to 4.8(6H, m); 7.0 to 8.2(11H, m) |
| 76 | (thiophene) | —COOH | 185–6 | DMSO d₆: 3.85(2H, d, J=12 Hz); 4.45(2H, d, J=12Hz); 7.0 to 8.0 (11H, m); 10.0 (1H, exchangeable with D₂O) |

EXAMPLE 77

Ethyl 9-Hydroxymethyl-9H-xanthene-9-carboxylate

A mixture of 1.5 g (5.9 mmol) of ethyl 9H-xanthene-9-carboxylate in 20 ml of THF and 1.6 ml of DMPU under an inert atmosphere is cooled to −50° C. 4 ml (6.4 mmol) of BuLi (1.6 M in hexane) are added dropwise to this medium with stirring, and the medium is then left stirring for 10 minutes at −40° C. After allowing the reaction medium to warm to 10° C., a flow of formaldehyde generated from 5.4 g (0.18 mol) of sublimed paraformaldehyde entrained by a stream of nitrogen is bubbled in. After stirring for 2 hours at room temperature, the suspension is dispersed in 50 ml of water. The reaction medium is then extracted twice with 100 ml of ether. The combined organic phases are dried over Na₂SO₄. After evaporation, the residual oil is chromatographed on silica. Eluent: CH₂Cl₂. 1.1 g of a yellow oil are obtained (yield: 68%).

NMR (CDCl₃): 1.07 (3H, t, J=7.1 Hz); 2.38 (1H, t, J=7.4 Hz); 3.9 (2H, d, J=7.5 Hz); 4.1 (2H, q, J=7.1 Hz); 6.9–7.26 (8H, m).

(9-Hydroxymethyl-9H-xanthen-9-yl)methanol 1.1 g (3.8 mmol) of the ester prepared above in 10 ml of THF are added dropwise to a mixture of 0.18 g (4.7 mmol) of LiAlH₄ dispersed in 30 ml of THF and cooled by a bath of cardice. After stirring for 2 hours at room temperature, 20 ml of water are added cautiously to the reaction medium. This mixture is then extracted twice with 100 ml of EtOAc. The combined organic phases are dried over Na₂SO₄. After evaporating to dryness, 0.7 g of a yellow oil is obtained (yield: 75%).

NMR (CDCl₃): 1.36 (2H, m); 3.83 (4H, d, J=6.0 Hz); 6.95 (2H, t, J=7.9 Hz); 6.96 (2H, d, J=7.9 Hz); 7.11 (2H, t, J=7.9 Hz); 7.32 (2H, d, J=7.9 Hz).

Ethyl 2-(4-Chlorophenyl)spiro[1,3-dioxane-5,9'-xanthene]-2-carboxylate (Example 77)

0.3 ml of BF₃.OEt₂ is added dropwise to a mixture of 1 g (4.7 mmol) of ethyl para-chlorophenyloxoacetate and 0.7 g of the diol prepared above in 20 ml of CH₂Cl₂, stirred at room temperature. After stirring for 2 hours at room temperature, the reaction medium is washed twice with 20 ml of saturated NaHCO₃. The organic phase is dried over Na₂SO₄ and then evaporated. The residual oil is chromatographed on a column of silica and eluted with an EtoAc/cyclohexane mixture (1:9). 0.4 g of whitish crystals is obtained and this product is recrystallized from acetone. 0.32 g of white crystals is collected (yield: 25%). m.p.= 131–132° C.

EXAMPLE 78

2-(4-Chlorophenyl)spiro[1,3-dioxane-5,9'-xanthene]-2-carboxylic Acid

A mixture of 0.09 g (0.2 mmol) of the ester prepared in Example 77, Example [sic], 0.5 g (9 mmol) of KOH, 20 ml of ethanol and 10 ml of water is stirred at reflux for 3 h. After cooling, the reaction medium is acidified with concentrated HCl solution to pH=5 and extracted with ethyl acetate. The combined organic phases are dried over Na₂SO₄ and then evaporated. The residual oil is crystallized from a suitable solvent. 0.06 g of white solid is isolated (yield=64%). m.p.=244–246° C.

EXAMPLE 79

(5-Hydroxymethyl-5H-dibenzo[a,d]cyclohepten-5-yl)methanol

A mixture of 11 g (0.05 mol) of 5H-dibenzo[a,d]cycloheptene-5-carboxaldehyde (prepared according to L. SALISBURY, J. Org. Chem., 1972, 37, 4075), 66 ml of ethanol, 16.2 ml (0.2 mol) of aqueous 37% formaldehyde solution, 11 ml of water and 6.6 g (0.05 mol) of K₂CO₃ is refluxed for 20 hours. The reaction medium is then poured into 1 liter of water with stirring and the mixture is extracted with CH₂Cl₂. The combined organic phases are dried over Na₂SO₄ and evaporated. The residual mass is triturated from 60 ml of absolute ethanol and disperses as a beige-coloured solid, which is filtered off and dried. 5 g of product are obtained (yield: 40%).

m.p.=162–163° C. NMR (DMSO d₆): 3.9–5 (4H, m); 7 (2H, s); 7.2–7.5 (8H, m).

Ethyl 2-(4-Chlorophenyl)spiro[1,3-dioxane-5,5'-5'H-dibenzo[a,d]cycloheptene]-2-carboxylate (Example 79)

A mixture of 2.9 g (15 mmol) of para-toluenesulphonic acid monohydrate and 500 ml of toluene in a reactor fitted with Dean-Stark apparatus is refluxed until the water has been completely removed. 12.6 g (0.05 mol) of the diol prepared above and 16 g (75 mmol) of ethyl para-chlorophenyloxoacetate are then added. The mixture is refluxed for 8 hours. After cooling, the reaction medium is washed with 300 ml of saturated aqueous NaHCO$_3$ solution and then with 300 ml of water. The organic phase is dried over Na$_2$SO$_4$ and then evaporated. The residual oil is chromatographed on a column of silica and eluted with a 5/95 EtOAc/cyclohexane mixture. The product is then washed with isopropyl ether and dried. 3 g of a white solid are obtained (yield: 14%). m.p.=206–208° C.

EXAMPLE 80

2-(4-Chlorophenyl)spiro[1,3-dioxane-5,5'-5'H-dibenzo[a,d]cycloheptene]-2-carboxylic Acid A mixture of 0.6 g (8 mmol) of potassium hydroxide, 17 ml of water, 70 ml of ethanol and 1.8 g (4 mmol) of the ester prepared according to Example 12 is refluxed for 5 hours. The solvent is then evaporated off. The resulting gum is dissolved in 50 ml of water and this aqueous phase is washed with ether and then acidified. The aqueous phase is extracted with CH$_2$Cl$_2$. The combined organic phases are dried over Na$_2$SO$_4$ and then evaporated. The residue is recrystallized from a suitable solvent. 1.1 g of a white solid are obtained (yield: 65%). m.p.>260° C.

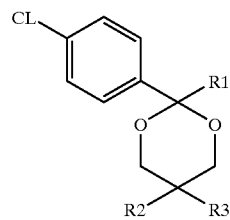

| Examples | R2 R3 | R1 | m.p. ° C. | NMR |
|---|---|---|---|---|
| 77 | (dibenzofuran-like structure with O bridge) | COOEt | 131–132 | CDCl$_3$: 1.2(3H, t, J=7.1Hz); (2H, d, J=12.1 Hz); 4.22(2H, q, J=7.1Hz); 4.35 (2H, d, J =12.1 Hz); 6.88–7.09(4H, m); 7.13–7.25(2H, m); 7.33(2H, d, J= 8.6Hz); 7.53–7.63(3H, m); 7.74 (1H, d, J=7.9 Hz) |
| 78 | (dibenzocycloheptene structure) | COOH | 244–246 | DMSO d$_6$: 4.28(2H, d, J=12.1Hz); 4.47(2H, d, J= 12.1Hz); 7.07–7.47(3H, m); 7.78 (6H, m); 7.91–8.05 (3H, m) |
| 79 | (dibenzocycloheptene structure) | COOC$_2$H$_5$ | 206–208 | CDCl$_3$: 1.1(3H, t, J=7Hz); 3.8 (1H, d, J=11.5 Hz); 4.1(2H, q, J= 7Hz); 4.7(1H, d, J=11.5Hz); 4.8(1H, d, J= 11.5Hz); 5.2(1H, d, J=11.5Hz); 7 (2H, s); 7.2–7.5 (12H, m) |
| 80 | (4-iodophenyl dioxane structure) | COOH | >260 | DMSO d$_6$: 3.5(1H, d, J=12Hz); 4.6 (1H, d, J=12 Hz); 4.7(1H, d, J= 12Hz); 5.5(1H, d, J=12 Hz); 7.1 (2H, s); 7.2–7.65 (12H, m); 13.5 (1H, s, exchangeable with CF$_3$COOD) |

EXAMPLE 81

2-(4-Chlorophenyl)-5,5-diphenyl[1,3]oxazinane

This product is obtained by reacting 3-amino-2,2-diphenyl-1-propanol with 4-chlorobenzaldehyde in refluxing toluene in the presence of p-toluenesulphonic acid for 5 hours.

The usual work-up allows the product to be obtained:

m.p.=169–170° C.; NMR (CDCl$_3$): 1.72 (1H, exchangeable with D$_2$O); 3.69 to 4.25 (3H, m); 4.9 to 4.96 (1H, m); 5.31 (1H, s); 7.19 to 7.6 (14H, m).

What is claimed is:
1. Compound of formula I:

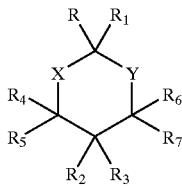

in which X and Y each represent an oxygen atom;

R represents a hydrogen atom; a (C$_1$–C$_7$)alkyl group; a phthalmido(C$_1$–C$_7$)alkyl group; (C$_3$–C$_{12}$)cycloalkyl; a group —(CH$_2$)$_p$—COOR$_b$ in which p is an integer from 0 to 6 and R$_b$ represents a hydrogen atom or a (C$_1$–C$_7$) alkyl group; a (C$_6$–C$_{10}$)aryl group; a 3- to 10-membered heterocycle comprising 1 to 4 endocyclic hetero atoms chosen from O, S and N; a (C$_6$–C$_{10}$)aryl(C$_1$–C$_7$)alkyl group; it being understood that the aryl groups present in R and the said heterocycle are optionally substituted with one or more substituents chosen from a radical Z as defined below and a (C$_1$–C$_7$)alkylene chain;

R$_1$ represents a hydrogen atom; a (C$_1$–C$_7$)alkyl group; (C$_1$–C$_7$)hydroxyalkyl; a (C$_6$–C$_{10}$)aryl group optionally substituted with one or more radicals W as defined below; a group —P(O)(OR$_8$)(OR$_9$) in which R$_8$ and R$_9$ are, independently, a hydrogen atom or a (C$_1$–C$_7$)alkyl group; a group —(CH$_2$)$_t$—COOR$_c$ in which t is an integer from 0 to 6 and R$_c$ represents a hydrogen atom or a (C$_1$–C$_7$) alkyl group; a group —CONR$_{10}$R$_{11}$ in which R$_{10}$ and R$_{11}$ independently represent a hydrogen atom, a (C$_1$–C$_7$)alkyl group, a group R$_d$O—CO—(C$_1$–C$_7$)alkyl in which R$_d$ represents h or (C$_1$–C$_7$)alkyl, or alternatively R$_{10}$ and R$_{11}$ together form a —(CH$_2$)$_r$— chain in which r is an integer equal to 4, 5 or 6;

R$_2$ and R$_3$ independently represent (C$_6$–C$_{10}$)aryl; (C$_6$–C$_{10}$)aryl(C$_1$–C$_7$)alkyl; a 3- to 10-membered heterocycle comprising 1 to 4 endocyclic hetero atoms chosen from O, N, and S; or a fluorenyl group; the said aryl groups present in R$_2$ or R$_3$, the said fluorenyl optionally being substituted with one or more radicals Z as defined below;

or alternatively R$_2$ and R$_3$ together form a chain —(CH$_2$)$_{r1}$— in which r1 is an integer equal to 2, 3, 4 or 5;

or alternatively R$_2$ and R$_3$ together form the group (a):

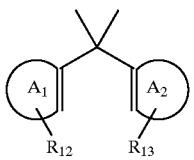

in which A$_1$ and A$_2$ independently represent (C$_6$–C$_{10}$) aryl or a 5- to 10-membered aromatic heterocycle comprising 1 to 4 endocyclic hetero atoms chosen from N, O, and S, the said aryl group and the said heterocycle optionally bearing, in addition to the substituents R$_{12}$ and R$_{13}$, one or more other substituents chosen from the radicals Z as defined below; and in which R$_{12}$ and R$_{13}$ together form a chain —(CH$_2$)$_m$—E—(CH$_2$)$_n$— or CHR$_{14}$=CHR$_{15}$— in which m and n are, independently, an integer from 0 to 6; E represents a bond, O, S, —NR$_e$—, in which R$_e$ represents a hydrogen atom or (C$_1$–C$_7$)alkyl or alternatively E represents a (C$_1$–C$_7$)alkylene or (C$_6$–C$_{10}$)arylene chain or a 3- to 10-membered divalent heterocyclic radical comprising 1 to 4 endocyclic hetero atoms chosen from O, N, and S; and R$_{14}$ and R$_{15}$ are chosen, independently from a hydrogen atom, (C$_1$–C$_7$)alkyl and (C$_6$–C$_{10}$)aryl;

R$_4$, R$_5$, R$_6$ and R$_7$ independently represent a hydrogen atom; (C$_1$–C$_7$)alkyl; (C$_6$–C$_{10}$)aryl optionally substituted with one or more radicals Z as defined below; or a 3- to 10-membered heterocycle comprising 1 to 4 endocyclic hetero atoms chosen from O, N and S, the said heterocycle optionally being substituted with one or more radicals Z as defined below;

is chosen from a halogen atom; a hydroxyl group; nitro; cyano; phenyl; phenyl(C$_1$–C$_7$)alkyl; trifluoromethoxy; (C$_1$–C$_7$)alkyl optionally substituted with one or more halogen atoms; (C$_1$–C$_7$)alkoxy; (C$_1$–C$_7$)alkylthio; (C$_1$–C$_7$)acylthio; (C$_1$–C$_7$)alkylsulphonyl; (C$_1$–C$_7$) alkylsulphinyl; carbamoyl; N—(C$_1$C$_7$)alkylcarbamoyl; N,N-di(C$_1$–C$_7$)alkylcarbamoyl; (C$_1$–C$_7$)alkylamino; di(C$_1$–C$_7$)alkylamino; a group —A—COOR$_d$ in which R$_d$ represents a hydrogen atom or a (C$_1$–C$_7$)alkyl group and A represents (C$_1$–C$_7$)alkylene; (C$_2$–C$_7$)alkenylene; (C$_1$–C$_7$)oxyalkylene in which the alkylene chain is linked to the group COOR$_f$ or alternatively A is nothing; or a group —B—P(O)(OR$_x$)(OR$_y$) in which B takes one of the meanings given for A above and R$_x$ and R$_y$ independently take one of the meanings for R$_f$ above;

W represents —G—COOR$_g$ in which G represents (C$_1$–C$_7$)alkylene, (C$_1$–C$_7$)alkenylene, (C$_1$–C$_7$) oxyalkylene in which the alkylene chain is linked to the group COOR$_g$ or alternatively G is nothing, and R$_g$ represents a hydrogen atom or a (C$_1$–C$_7$)alkyl group; or alternatively W represents —D—P(O)(OR$_z$)(OR$_c$) in which D takes one of the meanings given for G and R$_z$ and R$_c$ independently take one of the meanings given above for R$_g$;

and the pharmaceutically acceptable salts thereof,
it being understood that
(i) when R$_2$, R$_3$, R$_5$ and R$_7$ represent a hydrogen atom, X and Y represent an oxygen atom; R$_4$ represents methyl; and R$_6$ represents a hydrogen atom or a methyl group, then $R_1$ and R, together with the carbon atom which bears them, do not form any of the following divalent radicals:

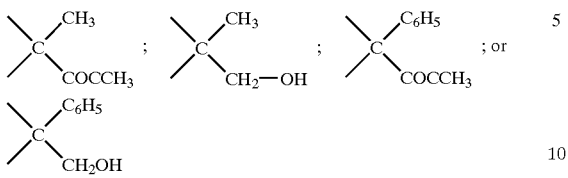

and (ii) when $R_4$, $R_5$, $R_6$ and $R_7$ represent a hydrogen atom; X and Y represent O; and r represents pyridyl, piperidyl or substituted piperidyl; then $R_1$ does not represent optionally substituted phenyl,
with the proviso that at least one of the radicals R or $R_1$ bears a carboxylic group optionally in esterified form or in the form of amide.

2. Compound of formula I according to claim 1, in which $R_4$, $R_5$, $R_6$ and $R_7$ represent a hydrogen atom.

3. Compound of formula I according to claim 1, in which:

R represents a hydrogen atom; a $(C_1–C_7)$alkyl group; a phthalamido $(C_1–C_7)$alkyl group; $(C_3–C_{12})$cycloalkyl; a heterocycle as defined in claim 1; a $(C_6–C_{10})$aryl group; or a $(C_6–C_{10})$aryl$(C_1–C_7)$alkyl group; it being understood that the aryl groups present in R and the said heterocycle are optionally substituted with one or more substituents chosen from a $(C_1–C_7)$alkylene chain; a halogen atom; a phenyl group; $(C_1–C_7)$ alkyl optionally substituted with one or more halogen atoms; $(C_1–C_7)$alkoxy; or a group —A—COORf in which A and Rf are as defined in claim 1;

$R_1$ represents a hydrogen atom; a $(C_1–C_7)$alkyl group; —$(CH_2)_t$—COORc in which t and Rc are as defined in claim 1;

$R_2$ and $R_3$ independently represent a hydrogen atom; a group $(C_6–C_{10})$aryl or $(C_6–C_{10})$aryl$(C_1–C_7)$alkyl; the aryl groups present in $R_2$ and $R_3$ optionally being substituted with one or more radicals chosen from a halogen atom; a $(C_1–C_7)$alkyl group optionally substituted with one or more halogen atoms; $(C_1–C_7)$ alkoxy; N—$(C_1–C_7)$alkyl-carbamoyl; $(C_1–C_7)$alkylamino; nitro; cyano; and —A—COORf in which A and Rf are as defined in claim 1;

or alternatively $R_2$ and $R_3$ together form the group (a) as defined in claim 1 in which $A_1$ and $A_2$ represent a phenyl group; and $R_{12}$ and $R_{13}$ together form a chain —$(CH_2)_m$—E—$(CH_2)_n$— in which m, n and E are as defined in claim 1, or a chain —$CHR_{14}$=$CHR_{15}$— in which $R_{14}$ and $R_{15}$ are as defined in claim 1; or alternatively $R_2$ and $R_3$ together form a chain —$(CH_2)_{r1}$— in which $r_1$ is an integer equal to 2, 3, 4 or 5.

4. Compound of formula I according to claim 1, in which:

R represents a hydrogen atom; a $(C_1–C_7)$alkyl group; $(C_3–C_{12})$cycloalkyl; —$(CH_2)_p$—$COOR_b$ in which p and $R_b$ are as defined in claim 1; —$(C_6–C_{10})$aryl or a heterocycle as defined in claim 1; it being understood that the said aryl group and the said heterocycle are optionally substituted with one or more substituents chosen from a halogen atom; a $(C_2–C_7)$alkyl group; $(C_1–C_7)$alkoxy; or —A—COORf in which A and Rf are as defined in claim 1;

$R_1$ represents a $(C_1–C_7)$alkyl or —$(CH_2)_t$—$COOR_c$ group in which t and $R_c$ are as defined in claim 1; a group —$CONR_{10}R_{11}$ in which $R_{10}$ and $R_{11}$ are as defined in claim 1;

$R_2$ and $R_3$ together form the group (a) as defined in claim 1 in which $A_1$ and $A_2$ represent phenyl; and $R_{12}$ and $R_{13}$ together form a chain —$(CH_2)_m$—E—$(CH_2)_n$— in which m and n represent 0 and E represents a bond.

5. Compound of formula I according to claim 1, in which

R represents $(C_6–C_{10})$aryl optionally substituted with a halogen atom;

$R_1$ represents —$COOR_c$ in which $R_c$ is as defined in claim 1;

$R_2$ and $R_3$ together form the group (a) as defined in claim 1 in which $A_1$ and $A_2$ represent phenyl; and $R_{12}$ and $R_{13}$ together form a chain —$(CH_2)_m$—E—$(CH_2)_n$— in which m and n represent 0 and E represents a bond, O or S.

6. Compound of formula I according to claim 1, in which

R represents $(C_6–C_{10})$aryl optionally substituted with a halogen atom;

$R_1$ represents —$COOR_c$ in which $R_c$ is as defined in claim 1;

$R_2$ and $R_3$ together form the group (a) as defined in claim 1 in which $A_1$ and $A_2$ represent phenyl; and $R_{12}$ and $R_{13}$ together form a chain —$CHR_{14}$=$CHR_{15}$— in which $R_{14}$ and $R_{15}$ are as defined in claim 1.

7. Compound of formula I according to claim 1, chosen from ethyl 2-(4-chlorophenyl)-5,5-diphenyl[1,3]-dioxane-2-carboxylate, 2-(4-chlorophenyl)-5,5-diphenyl-[1,3]dioxane-2-carboxylic acid, ethyl 2,5,5-tris(4-chlorophenyl)-[1,3]dioxane-2-carboxylate, 2,5,5-tris(4-chlorophenyl)-[1,3]dioxane-2-carboxylic acid, ethyl 2-(4-chlorophenyl)spiro[[1,3]dioxane-5,9'-fluorene]-2-carboxylate, 2-(4-chlorophenyl)spiro[[1,3]dioxane-5,9'-fluorene]-2-carboxylic acid.

8. A process for preparing a compound of formula I, according to claim 1, comprising reacting a compound of formula:

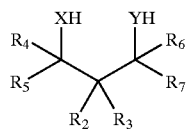

in which X, Y and $R_2$ to $R_7$ are as defined in claim 1, with a carbonyl derivative of formula III:

RCO—$R_1$    III in which R and $R_1$ are as defined in claim 1.

9. A process for preparing a compound of formula I according to claim 1, in which X and Y each represent an oxygen atom, comprising reacting an alkali metal or alkaline-earth metal salt of a diol of formula II

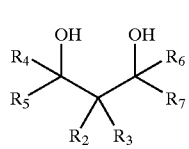

in which $R_2$ to $R_7$ are as defined in claim 1, with a dihalo compound of formula IV

IV in which R and $R_1$ are as defined in claim 1 and X represents a halogen atom.

10. A diol chosen from 2,2-bis(4-flurophenyl) propane-1,3 diol;

2,2-bis(3-trifluoromethylphenyl) propane-1,3 diol;

5-hydroxymethyl-5H-dibenzo[a,d]cyclohepten-5-ylmethanol; and (9-hydroxymethyl-9H-xanthen-9-yl)methanol.

11. A pharmaceutical composition comprising an effective amount of at least one compound according to claim 1 and a compound of formula I as defined in (i) in claim 1, in combination with at least one pharmaceutically acceptable vehicle.

12. A composition according to claim 11, in the form of an immediate-release tablet, a controlled-release tablet, a gelatin capsule, an injectable solution or a cream.

13. A method for preventing or treating dyslipidaemia, atherosclerosis, and diabetes comprising administering to a patient an effective amount of a compound of formula I according to claim 1, and a compound of formula I as defined in (i) or (ii) in claim 1.

14. A pharmaceutical composition according to claim 11, comprising an effective amount of at least one compound of formula I as defined in (i) in claim 12, in combination with at least one pharmaceutically acceptable vehicle.

15. The method according to claim 13, comprising administering to a patient an effective amount of a compound of formula I as defined in (i) in claim 13.

\* \* \* \* \*

UNITED STATES PATENT AND TRADEMARK OFFICE
CERTIFICATE OF CORRECTION

PATENT NO. : 6,528,538 B1
DATED : March 4, 2003
INVENTOR(S) : Jean-Jacques Zeiller et al.

It is certified that error appears in the above-identified patent and that said Letters Patent is hereby corrected as shown below:

Title page,
Item [54], Title, "PHARAMACEUTICAL" should read -- PHARMACEUTICAL --

Column 55,
Line 35, reads "phthalmido" should read -- phthalamido --
Line 55, reads "represents h" should read -- represents H --
Line 63, reads "the said fluorenyl" should read -- the said heterocycle and the said fluorenyl --

Colunm 56,
Line 37, reads "is chosen" should read -- Z is chosen --
Line 42, reads "($C_1$-$C_7$)acylthio;" should read -- ($C_2$-$C_7$)acylthio; --
Line 43, reads "($C_1$-$C_7$)alkylcarbamoyl;" should read -- ($C_1$-$C_7$)alkylcarbamoyl --
Line 55, reads "($C_1$-$C_7$)alkenylene," should read -- ($C_2$-$C_7$)alkenylene, --
Line 60, reads "($OR_c$)" should read -- ($OR_t$) --
Line 61, reads "$R_c$ independently" should read -- $R_t$ independently --

Column 57,
Line 8, reads "$COCCH_3$" should read -- $COOCH_3$ --
Line 14, reads "and r represents" should read -- and R represents --
Line 61, reads reads "a ($C_2$-$C_7$)alkyl group;" should read -- a ($C_1$-$C_7$)alkyl group; --

Column 59,
Lines 17-18, reads "one compound according to claim 1 and a compound of formula I as defined in (i) in claim 1," should read -- one compound of formula I as defined in (i) or (ii) according to claim 1, --

Column 60,
Lines 8-9, reads "according to claim 1, and a compound of formula I as defined in (i) or (ii) in claim I." should read -- as defined in (i) or (ii) according to claim 1. --

UNITED STATES PATENT AND TRADEMARK OFFICE
CERTIFICATE OF CORRECTION

PATENT NO.     : 6,528,538 B1
DATED          : March 4, 2003
INVENTOR(S)    : Jean-Jacques Zeiller et al.

It is certified that error appears in the above-identified patent and that said Letters Patent is hereby corrected as shown below:

Column 60 (cont'd),
Line 12, reads "as defined in (i) in claim 12," should read -- as defined in (i) in claim 11, --

Signed and Sealed this

Twenty-seventh Day of July, 2004

JON W. DUDAS
*Acting Director of the United States Patent and Trademark Office*